US007874985B2

(12) United States Patent
Kovatchev et al.

(10) Patent No.: US 7,874,985 B2
(45) Date of Patent: Jan. 25, 2011

(54) METHOD, SYSTEM, AND COMPUTER PROGRAM PRODUCT FOR THE EVALUATION OF GLYCEMIC CONTROL IN DIABETES FROM SELF-MONITORING DATA

(75) Inventors: Boris P. Kovatchev, Amherst, VA (US); Daniel J. Cox, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1307 days.

(21) Appl. No.: 11/305,946

(22) Filed: Dec. 19, 2005

(65) Prior Publication Data
US 2006/0094947 A1 May 4, 2006

Related U.S. Application Data

(62) Division of application No. 10/240,228, filed as application No. PCT/US01/09884 on Mar. 29, 2001, now Pat. No. 7,025,425.

(60) Provisional application No. 60/193,037, filed on Mar. 29, 2000.

(51) Int. Cl.
*A61B 5/00* (2006.01)
*A61B 5/05* (2006.01)
(52) U.S. Cl. .................... 600/365; 600/347
(58) Field of Classification Search ............ 600/347, 600/365
See application file for complete search history.

(56) References Cited

U.S. PATENT DOCUMENTS

| 4,695,954 A | 9/1987 | Rose et al. |
| 4,731,726 A | 3/1988 | Allen, III |
| 4,779,199 A | 10/1988 | Yoneda et al. |
| 4,817,044 A | 3/1989 | Ogren |
| 5,019,974 A | 5/1991 | Beckers |

(Continued)

FOREIGN PATENT DOCUMENTS

EP  0 462 466 B1  12/1991

(Continued)

OTHER PUBLICATIONS

F. John Service, M.D., et al., "Mean Amplitude of Glycemic Excursions, a Measure of Diabetic Instability", Diabetes, vol. 19, No. 9, Sep. 1970, pp. 644-655.

(Continued)

*Primary Examiner*—Patricia C Mallari
(74) *Attorney, Agent, or Firm*—Novak Druce DeLuca + Quigg LLP; Robert J. Decker

(57) ABSTRACT

A method, system, and computer program product related to the diagnosis of diabetes, and is directed to predicting the long-term risk of hyperglycemia, and the long-term and short-term risks of severe hypoglycemia in diabetics, based on blood glucose readings collected by a self-monitoring blood glucose device. The method, system, and computer program product pertain directly to the enhancement of existing home blood glucose monitoring devices, by introducing an intelligent data interpretation component capable of predicting both $HbA_{1c}$ and periods of increased risk of hypoglycemia, and to the enhancement of emerging continuous monitoring devices by the same features. With these predictions the diabetic can take steps to prevent the adverse consequences associated with hyperglycemia and hypoglycemia.

36 Claims, 9 Drawing Sheets

U.S. PATENT DOCUMENTS

| | | | |
|---|---|---|---|
| 5,216,597 A | 6/1993 | Beckers |
| 5,251,126 A | 10/1993 | Kahn et al. |
| 5,307,263 A | 4/1994 | Brown |
| 5,319,363 A | 6/1994 | Welch et al. |
| 5,341,291 A | 8/1994 | Roizen et al. |
| 5,376,070 A | 12/1994 | Purvis et al. |
| 5,500,854 A | 3/1996 | Uotila |
| 5,558,638 A | 9/1996 | Evers et al. |
| 5,590,648 A | 1/1997 | Mitchell et al. |
| 5,626,144 A | 5/1997 | Tacklind et al. |
| 5,704,366 A | 1/1998 | Tacklind et al. |
| 5,713,856 A | 2/1998 | Eggers et al. |
| 5,772,586 A | 6/1998 | Heinonen et al. |
| 5,878,384 A | 3/1999 | Johnson et al. |
| 5,925,021 A | 7/1999 | Castellano et al. |
| 5,946,659 A | 8/1999 | Lancelot et al. |
| 5,960,403 A | 9/1999 | Brown |
| 5,974,389 A | 10/1999 | Clark et al. |
| 5,997,476 A | 12/1999 | Brown |
| 6,022,315 A | 2/2000 | Iliff |
| 6,024,699 A | 2/2000 | Surwit et al. |
| 6,049,764 A | 4/2000 | Stahl |
| 6,081,786 A | 6/2000 | Barry et al. |
| 6,134,504 A | 10/2000 | Douglas et al. |
| 6,144,922 A | 11/2000 | Douglas et al. |
| 6,188,988 B1 | 2/2001 | Barry et al. |
| 6,206,829 B1 | 3/2001 | Iliff |
| 6,225,901 B1 | 5/2001 | Kail, IV |
| 6,234,964 B1 | 5/2001 | Iliff |
| 6,270,455 B1 | 8/2001 | Brown |
| 6,277,071 B1 | 8/2001 | Hennessy et al. |
| 6,336,900 B1 | 1/2002 | Alleckson et al. |
| 6,338,713 B1 | 1/2002 | Chamoun et al. |
| 6,352,505 B1 | 3/2002 | Bortz |
| 6,368,273 B1 | 4/2002 | Brown |
| 6,379,301 B1 | 4/2002 | Worthington et al. |
| 6,406,426 B1 | 6/2002 | Reuss et al. |
| 6,418,346 B1 | 7/2002 | Nelson et al. |
| 6,421,633 B1 * | 7/2002 | Heinonen et al. | 703/11 |
| 6,422,061 B1 | 7/2002 | Sunshine et al. |
| 6,450,956 B1 | 9/2002 | Rappaport et al. |
| 6,524,240 B1 | 2/2003 | Thede |
| 6,540,672 B1 | 4/2003 | Simonsen et al. |
| 6,544,174 B2 | 4/2003 | West et al. |
| 6,544,212 B2 | 4/2003 | Galley et al. |
| 6,551,243 B2 | 4/2003 | Bocionek et al. |
| 6,558,351 B1 | 5/2003 | Steil et al. |
| 6,575,900 B1 | 6/2003 | Zweig et al. |
| 6,579,231 B1 | 6/2003 | Phipps et al. |
| 6,604,050 B2 | 8/2003 | Trippel et al. |
| 6,611,846 B1 | 8/2003 | Stoodley |
| 6,635,016 B2 | 10/2003 | Finkelshteins |
| 6,645,142 B2 | 11/2003 | Braig et al. |
| 6,656,114 B1 | 12/2003 | Poulsen et al. |
| 6,692,436 B1 | 2/2004 | Bluth et al. |
| 6,781,522 B2 | 8/2004 | Sleva et al. |
| 6,799,149 B2 | 9/2004 | Hartlaub |
| 6,804,558 B2 | 10/2004 | Haller et al. |
| 6,872,200 B2 | 3/2005 | Mann et al. |
| 6,915,170 B2 | 7/2005 | Engleson et al. |
| 2003/0216628 A1 | 11/2003 | Bortz et al. |
| 2005/0187789 A1 | 8/2005 | Hatlestad et al. |
| 2005/0267780 A1 | 12/2005 | Ray et al. |
| 2006/0010098 A1 | 1/2006 | Goodnow et al. |
| 2006/0106644 A1 | 5/2006 | Koo et al. |
| 2006/0173260 A1 | 8/2006 | Gaoni et al. |
| 2006/0189863 A1 | 8/2006 | Peyser et al. |
| 2007/0033074 A1 | 2/2007 | Nitzan et al. |

FOREIGN PATENT DOCUMENTS

| | | |
|---|---|---|
| GB | 2159625 A | 12/1985 |

OTHER PUBLICATIONS

J. Schlichtkrull et al., "The M-Value, an Index of Blood-sugar Control in Diabetics", Acta Medica Scandinavica, vol. 177, fasc. 1, 1965, pp. 95-102.

David Rodbard, M.D., "Optimizing Display Analysis, Interpretation and Utility of Self-Monitoring of Blood Glucose (SMBG) Data for Management of Patients with Diabetes", Journal of Diabetes Science and Technology, vol. 1, Issue 1, Jan. 2007, pp. 62-71.

Accu-Check Camit Pro User's Manual, Roche Diagnostics, 2005, 220 pages.

Edmond A. Ryan et al. "Assessment of the Severity of Hypoglycemia and Glycemic Lability in Type 1 Diabetic Subjects Undergoing Islet Transplantation", , Diabetes, vol. 53, Apr. 2004, pp. 955-962.

Boris P. Kovatchev et al., "Evaluation of a New Measure of Blood Glucose Variability in Diabetes", Diabetes Care, vol. 29, No. 11, Nov. 2006, pp. 2433-2438.

Michael Brownlee, MD et al., "Glycemic Variabiity: A Hemoglobin $A_{1c}$-Independent Risk Factor for Diabetic Complications", (reprinted) JAMA, vol. 295, No. 14, Apr. 12, 2006, pp. 1707-1708.

Irl B. Hirsch, M.D. "Glycemic Variability: It's Not Just about A1C Anymore!", Diabetes Technology & Therapeutics, 2005, pp. 780-783, vol. 7, No. 5.

Boris P. Kovatchev, et al., Methods for Quantifying Self-Monitoring Blood Glucose Profiles Exemplified by an Examination of Blood Glucose Patterns in Patients with Type 1 and Type 2 Diabetes Technology & Therapeutics, 2002, pp. 295-303, vol. 4, No. 3.

Louis Monnier et al., "Activation of Oxidative Stress by Acute Glucose Fluctuations Compared with Sustained Chronic Hyperglycemia in Patients with Type 2 Diabetes", JAMA, Apr. 12, 2006, pp. 1681-1687, vol. 295, No. 14.

David Rodbard, "Improved Methods for Calculating a Figure of Merit" for Blood Glucose Monitoring Data, Diabetes Technology Meeting, San Francisco, CA, Nov. 2005, 1 page.

J.M. Wojcicki, ""J"-Index. A New Proposition of the Assessment of Current Glucose Control in Diabetic Patients", Hormone and Metabolic Research, 1995, pp. 41-42, vol. 27.

* cited by examiner

METHOD, SYSTEM, AND COMPUTER PROGRAM PRODUCT FOR THE EVALUATION OF GLYCEMIC CONTROL IN DIABETES FROM SELF-MONITORING DATA

CROSS-REFERENCES TO RELATED APPLICATIONS

This application is divisional application of U.S. application Ser. No. 10/240,228, filed Sep. 26, 2002, now U.S. Pat. No. 7,025,425, which is a national stage filing of International Application No. PCT/US01/09884, filed on Mar. 29, 2001, which claims benefit under 35 U.S.C Section 119(e) from U.S. Provisional Patent Application Ser. No. 60/193,037 filed Mar. 29, 2000, entitled "Algorithm for the Evaluation of Glycemic Control in Diabetes From Self-Monitoring Data" the entire disclosures of which are hereby incorporated by reference herein in their entirety.

US GOVERNMENT RIGHTS

This invention was made with United States Government support under Grant Nos. NIH/NIDDK: RO1 DK 28288 and NIH/NIDDK: RO1 DK 51562, both awarded by National Institutes of Health. The United States Government has certain rights in the invention.

FIELD OF THE INVENTION

The present system relates generally to Glycemic Control of individuals with diabetes, and more particularly to a computer-based system and method for evaluation of predicting glycosylated hemoglobin ($HbA_{1c}$ and $HbA_1$) and risk of incurring hypoglycemia.

BACKGROUND OF THE INVENTION

Extensive studies, including the Diabetes Control and Complications Trial (DCCT) (See DCCT Research Group: The Effect Of Intensive Treatment Of Diabetes On The Development And Progression Of Long-Term Complications Of Insulin-Dependent Diabetes Mellitus. *New England Journal of Medicine*, 329: 978-986, 1993), the Stockholm Diabetes Intervention. Study (See Reichard P, Phil M: Mortality and Treatment Side Effects During Long-term Intensified Conventional Insulin Treatment in the Stockholm Diabetes Intervention Study. *Diabetes*, 43: 313-317, 1994), and the United Kingdom Prospective Diabetes Study (See UK Prospective Diabetes Study Group: Effect of Intensive Blood Glucose Control With Metformin On Complications In Patients With Type 2 Diabetes (UKPDS 34). *Lancet*, 352: 837-853, 1998), have repeatedly demonstrated that the most effective way to prevent the long term complications of diabetes is by strictly maintaining blood glucose (BG) levels within a normal range using intensive insulin therapy.

However, the same studies have also documented some adverse effects of intensive insulin therapy, the most acute of which is the increased risk of frequent severe hypoglycemia (SH), a condition defined as an episode of neuroglycopenia which precludes self-treatment and requires external help for recovery (See DCCT Research Group: Epidemiology of Severe Hypoglycemia In The Diabetes Control and Complications Trial. *American Journal of Medicine*, 90: 450-459, 1991, and DCCT Research Group: Hypoglycemia in the Diabetes Control and Complications Trial. *Diabetes*, 46: 271-286, 1997). Since SH can result in accidents, coma, and even death, patients and health care providers are discouraged from pursuing intensive therapy. Consequently, hypoglycemia has been identified as a major barrier to improved glycemic control (Cryer PE: Hypoglycemia is the Limiting Factor in the Management Of Diabetes. *Diabetes Metab Res Rev*, 15: 42-46, 1999).

Thus, patients with diabetes face a life-long optimization problem of maintaining strict glycemic control without increasing their risk of hypoglycemia. A major challenge related to this problem is the creation of simple and reliable methods that are capable of evaluating both patients' glycemic control and their risk of hypoglycemia, and that can be applied in their everyday environments.

It has been well known for more than twenty years that glycosylated hemoglobin is a marker for the glycemic control of individuals with Diabetes Mellitus (Type I or Type II). Numerous researchers have investigated this relationship and have found that glycosylated hemoglobin generally reflects the average BG levels of a patient over the previous two months. Since in the majority of patients with diabetes the BG levels fluctuate considerably over time, it was suggested that the real connection between integrated glucose control and $HbA_{1c}$ would be observed only in patients known to be in stable glucose control over a long period of time.

Early studies of such patients produced an almost deterministic relationship between the average BG level in the preceding 5 weeks and $HbA_{1c}$, and this curvilinear association yielded a correlation coefficient of 0.98 (See Aaby Svendsen P, Lauritzen T, Soegard U, Nerup J (1982). Glycosylated Hemoglobin and Steady-State Mean Blood Glucose Concentration in Type 1 (Insulin-Dependent) Diabetes, *Diabetologia*, 23, 403-405). In 1993 the DCCT concluded that $HbA_{1c}$ was the "logical nominee" for a gold-standard glycosylated hemoglobin assay, and the DCCT established a linear relationship between the preceding mean BG and $HbA_{1c}$ (See Santiago J V (1993). Lessons from the Diabetes Control and Complications Trial, *Diabetes*, 42, 1549-1554).

Guidelines were developed indicating that an $HbA_{1c}$ of 7% corresponds to a mean BG of 8.3 mM (150 mg/dl), an $HbA_{1c}$ of 9% corresponds to a mean BG of 11.7 mM (210 mg/dl), and a 1% increase in $HbA_{1c}$ corresponds to an increase in mean BG of 1.7 mM (30 mg/dl, 2). The DCCT also suggested that because measuring the mean BG directly is not practical, one could assess a patient's glycemic control with a single, simple test, namely $HbA_{1c}$. However, studies clearly demonstrate that $HbA_{1c}$ is not sensitive to hypoglycemia.

Indeed, there is no reliable predictor of a patient's immediate risk of SH from any data. The DCCT concluded that only about 8% of future SH could be predicted from known variables such-as-the-history of SH, low $HbA_{1c}$, and hypoglycemia unawareness. One recent review details the current clinical status of this problem, and provides options for preventing SH, that are available to patients and their health care providers (See Bolli, G B: How To Ameliorate The Problem of Hypoglycemia In Intensive As Well As Nonintensive Treatment Of Type I Diabetes. *Diabetes Care*, 22, Supplement 2: B43-B52, 1999).

Contemporary home BG monitors provide the means for frequent BG measurements through Self-Monitoring of BG (SMBG). However, the problem with SMBG is that there is a missing link between the data collected by the BG monitors, and $HbA_{1c}$ and hypoglycemia. In other words, there are currently no reliable methods for evaluating $HbA_{1c}$ and recognizing imminent hypoglycemia based on SMBG readings (See Bremer T and Gough D A: Is blood glucose predictable from previous values? A solicitation for data. *Diabetes* 48:445-451, 1999).

Thus, an object of this invention is to provide this missing link by proposing three distinct, but compatible, algorithms for evaluating $HbA_{1c}$ and the risk of hypoglycemia from SMBG data, to be used to predict the short-term and long-term risks of hypoglycemia, and the long-term risk of hyperglycemia.

The inventors have previously reported that one reason for a missing link between the routinely available SMBG data and the evaluation of $HbA_{1c}$ and the risk of hypoglycemia, is that the sophisticated methods of data collection and clinical assessment used in diabetes research, are infrequently supported by diabetes-specific and mathematically sophisticated statistical procedures.

Responding to the need for statistical analyses that take into account the specific distribution of BG data, the inventors developed a symmetrizing transformation of the blood glucose measurement scale (See Kovatchev B P, Cox D J, Gonder-Frederick L A and W L Clarke (1997). Symmetization of the Blood Glucose Measurement Scale and Its Applications, *Diabetes Care*, 20, 1655-1658) that works as the follows. The BG levels are measured in mg/dl in the United States, and in mmol/L (or mM) in most other countries. The two scales are directly related by 18 mg/dl=1 mM. The entire BG range is given in most references as 1.1 to 33.3 mM, and this is considered to cover practically all observed values. According to the recommendations of the DCCT (See DCCT Research Group (1993) The Effect Of Intensive Treatment of Diabetes On the Development and Progression of Long-Term Complications of Insulin-Dependent Diabetes Mellitus. *New England Journal of Medicine*, 329, pp 978-986) the target BG range—also known as the euglycemic range—for a person with diabetes is 3.9 to 10 mM, hypoglycemia occurs when the BG falls below 3.9 mM, and hyperglycemia is when the BG rises above 10 mM. Unfortunately, this scale is numerically asymmetric—the hyperglycemic range (10 to 33.3 mM) is wider than the hypoglycemic range (1.1 to 3.9 mM), and the euglycemic range (3.9 to 10 mM) is not centered within the scale. The inventors correct this asymmetry by introducing a transformation, f(BG), which is a continuous function defined on the BG range [1.1, 33.3], having the two-parameter analytical form:

$$f(BG,\alpha,\beta)=[(\ln(BG))^{\alpha}-\beta], \alpha,\beta>0$$

and which satisfies the assumptions:

$$f(33.3,\alpha,\beta)=-f(1.1,\alpha,\beta) \text{ and} \qquad\qquad A1$$

$$f(10.0,\alpha,\beta)=-f(3.9,\alpha,\beta). \qquad\qquad A2$$

Next, $f(.)$ is multiplied by a third scaling parameter to fix the minimum and maximum values of the transformed BG range at $-\sqrt{10}$ and $\sqrt{10}$ respectively. These values are convenient since a random variable with a standard normal distribution has 99.8% of its values within the interval $[-\sqrt{10},\sqrt{10}]$. If BG is measured in mmol/l, when solved numerically with respect to the assumptions A1 and A2, the parameters of the function $f(BG, \alpha, \beta)$ are $\alpha=1.026$, $\beta=1.861$, and the scaling parameter is $\gamma=1.794$. If BG is measured in mg/dl instead, the parameters are computed to be $\alpha=1.084$, $\beta=5.381$, and $\gamma=1.509$.

Thus, when BG is measured in mmol/l, the symmetrizing transformation is $f(BG)=1.794[(\ln(BG))^{1.026}-1.861]$. and when BG is measured in mg/dl the symmetrizing transformation is $f(BG)=1.509[(\ln(BG))^{1.084}-5.381]$.

On the basis of the symmetrizing transformation $f(.)$ the inventors introduced the Low BG Index—a new measure for assessing the risk of hypoglycemia from SMBG readings (See Cox D J, Kovatchev B P, Julian D M, Gonder-Frederick L A, Polonsky W H, Schlundt D G, Clarke W L: Frequency of Severe Hypoglycemia In IDDM Can Be Predicted From Self-Monitoring Blood Glucose Data. *Journal of Clinical Endocrinology and Metabolism*, 79: 1659-1662, 1994, and Kovatchev B P, Cox D J, Gonder-Frederick L A Young-Hyman D, Schlundt D, Clarke W L. Assessment of Risk for Severe Hypoglycemia Among Adults With IDDM: Validation of the Low Blood Glucose Index, *Diabetes Care* 21:1870-1875, 1998). Given a series of SMBG data the Low BG Index is computed as the average of $10.f(BG)^2$ taken for values of $f(BG)<0$ and 0 otherwise. Also suggested was a High BG Index, computed in a symmetrical to the Low BG Index manner, however this index did not find its practical application.

Using the Low BG Index in a regression model the inventors were able to account for 40% of the variance of SH episodes in the subsequent 6 months based on the SH history and SMBG data, and later to enhance this prediction to 46% (See Kovatchev B P, Straume M, Farhi L S, Cox D J: Estimating the Speed of Blood Glucose Transitions and its Relationship With Severe Hypoglycemia. *Diabetes*, 48: Supplement 1, A363, 1999).

In addition, the inventors developed some data regarding $HbA_{1c}$ and SMBG (See Kovatchev B P, Cox D J, Straume M, Farhy L S. Association of Self-monitoring Blood Glucose Profiles with Glycosylated Hemoglobin. *In: Methods in Enzymology vol. 321: Numerical Computer Methods, Part C*, Michael Johnson and Ludvig Brand, Eds., Academic Press, NY; 2000).

These developments became a part of the theoretical background of this invention. In order to bring this theory into practice, several key theoretical components, among other things, as described in the following sections, were added. In particular, three methods were developed for employing the evaluation of $HbA_{1c}$, long-term and short-term risk for hypoglycemia. The development of these methods was, but not limited thereto, based on detailed analysis of data for 867 individuals with diabetes that included more than 300,000 SMBG readings, records of severe hypoglycemia and determinations of $HbA_{1c}$.

The inventors have therefore sought to improve upon the aforementioned limitations associated with the conventional methods, and thereby provide simple and reliable methods that are capable of evaluating both patients' glycemic control and their risk of hypoglycemia, and that can be applied in their everyday environments.

SUMMARY OF THE INVENTION

The invention includes a data analysis method and computer-based system for the simultaneous evaluation, from routinely collected SMBG data, of the two most important components of glycemic control in diabetes: $HbA_{1c}$ and the risk of hypoglycemia. For the purposes of this document, self-monitoring of BG (SMBG) is defined as any method for determination of blood glucose at diabetic patients' natural environment and includes the methods used by contemporary SMBG devices customarily storing 200-250 BG readings, as well as methods used by emerging continuous monitoring technologies. Given this broad definition of SMBG, this invention pertains directly to the enhancement of existing home blood glucose monitoring devices by introducing an intelligent data interpretation component capable of predicting both $HbA_{1c}$ and periods of increased risk of hypoglycemia, as well as to enhancement of future continuous monitoring devices by the same features.

One aspect of the invention includes a method, system, and computer program product for evaluating $HbA_{1c}$ from a predetermined period of collected SMBG data, for example 4-6 weeks. In one embodiment, the invention provides a computerized method and system for evaluating the $HbA_{1c}$ of a patient based on BG data collected over a predetermined duration. The method includes computing weighted deviation toward high blood glucose (WR) and estimated rate of change of blood glucose (Dr) based on the collected BG data; estimating $HbA_{1c}$ using a predetermined mathematical formula based on the computed WR and Dr; and providing a predetermined confidence interval for classification of said estimated value of $HbA_{1c}$.

Another aspect of the invention includes a method, system, and computer program product for estimating the long-term probability for severe hypoglycemia (SH). This method uses SMBG readings from a predetermined period, for example 4-6 weeks, and predicts the risk of SH within the following 6 months. In one embodiment, the invention provides a computerized method and system for evaluating the long term probability for severe hypoglycemia (SH) of a patient based on BG data collected over a predetermined duration. The method includes: computing weighted deviation toward low blood glucose (WL) and estimated rate of fall of blood glucose in the low BG range (DrDn) based on the collected BG data; estimating the number of future SH episodes using a predetermined mathematical formula based on the computed WL and DrDn; and defining a probability of incurring a select number of SH episodes respective to said estimated SH episodes.

Still yet another aspect of the invention includes a method, system, and computer program product for identifying 24-hour periods (or other select periods) of increased risk of hypoglycemia. This is accomplished through the computation of the short-term risk of hypoglycemia using SMBG readings collected over the previous 24 hours. In one embodiment, the invention provides a computerized method and system for evaluating the short term risk for severe hypoglycemia (SH) of a patient based on BG data collected over a predetermined duration. The method includes: computing weighted deviation toward low blood glucose (WL); determining Max(wl) by calculating maximum value of wl(BG;2); determining risk value by taking the geometric mean of WL and Max(wl) over the predetermined duration; providing a predetermined threshold risk value; and comparing the determined risk value to the threshold risk value.

These three aspects of the invention can be integrated together to provide continuous information about the glycemic control of an individual with diabetes, and enhanced monitoring of the risk of hypoglycemia.

These and other objects, along with advantages and features of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which.

DETAILED DESCRIPTION OF THE INVENTION

Figure 1:
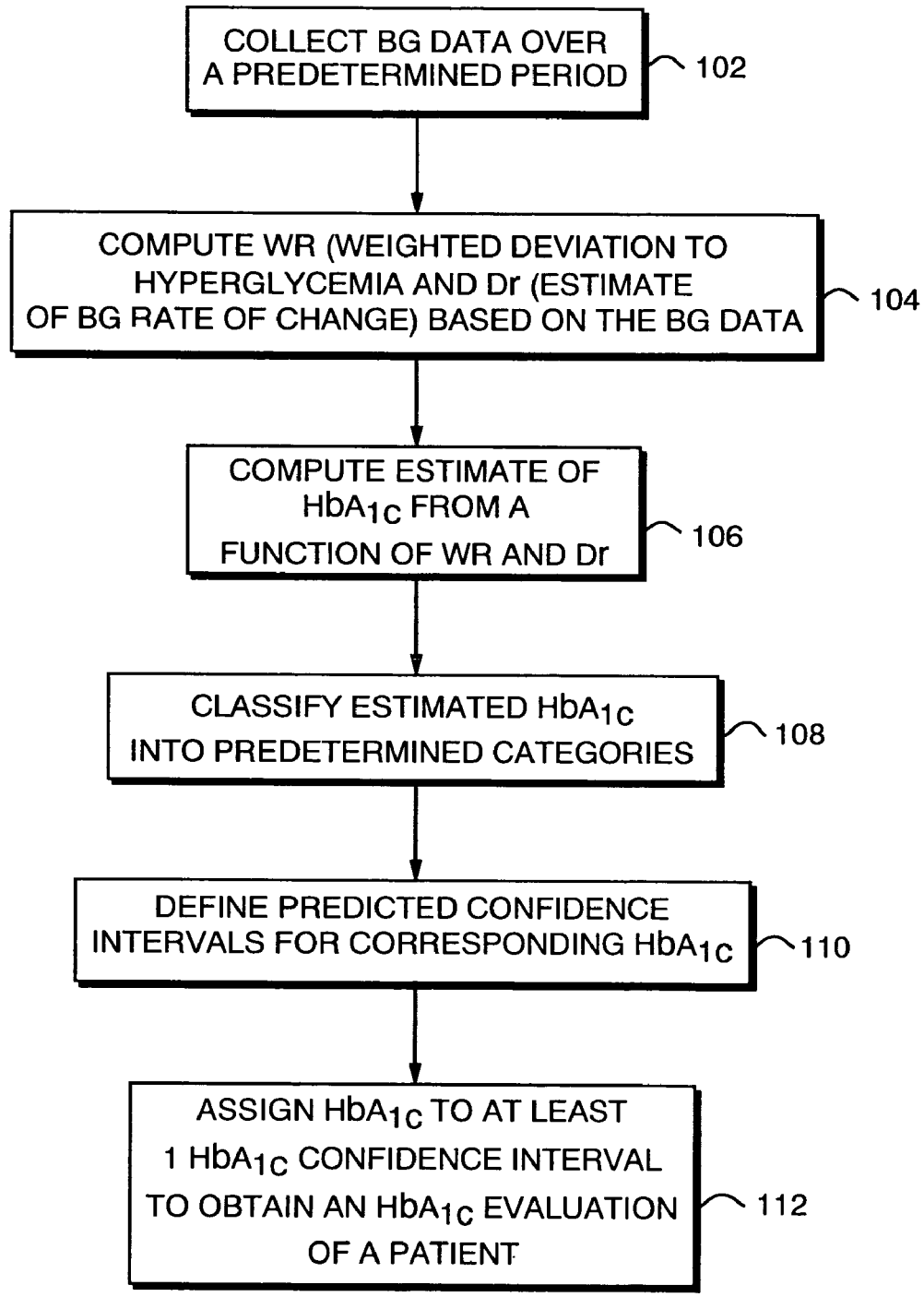
FIG. 1 is a flow chart illustrating the method of calculating the estimated $HbA_{1c}$ and predicted $HbA_{1c}$ confidence intervals in accordance with the present invention.

The invention makes possible, but not limited thereto, the creation of precise methods for the evaluation of diabetics' glycemic control, and include, firmware and software code to be used in computing the key components of the method. The inventive methods for evaluating $HbA_{1c}$, the long-term probability of SH, and the short-term risk of hypoglycemia, are also validated based on the extensive data collected, as will be discussed later in this document. Finally, the aspects of these methods can be combined in structured display or matrix.

Stationary Measures of BG Deviation

According to the inventors' theory of BG symmetrization (See Kovatchev B P, Straume M, Cox D J, Farhi L S. Risk Analysis of Blood Glucose Data: A Quantitative Approach to Optimizing the Control of Insulin Dependent Diabetes. *J of Theoretical Medicine*, 3:1-10, 2001) the natural clinical center of the BG measurement scale is at BG level of 112.5 mg/dl (6.25 mmol/l)—a safe euglycemic value for a diabetes patient.

Given this clinical center of the BG scale, the weighted deviations to the left (towards hypoglycemia) or to the right (towards hyperglycemia) are computed. The degree of weighting of these deviations will be represented by parameters a and b respectively as follows:

$wl(BG;a) = 10 \cdot f(BG)^a$ if $f(BG) < 0$ and 0 otherwise, and $wr(BG;b) = 10 \cdot f(BG)_b$ if $f(BG) > 0$ and 0 otherwise, where $f(BG)$ is the BG symmetrization function presented in the background section. The weighting parameter a and b could be different, or the same for the left and right deviations. The inventors' data analyses demonstrated that the optimal for practical application parameter values are a=2 (which is the parameter value used for computation of the Low BG Index) and b=1. Given a series of BG readings $x_1, x_2, \ldots x_n$, the average weighted deviations to the left and to the right of the clinical center of the BG scale are defined as:

$$WL = \frac{1}{n}\sum_{i=1}^{n} wl(x_i; 2) \text{ and } WR = \frac{1}{n}\sum_{i=1}^{n} wr(x_i; 1)$$

These two measures of BG deviation do not depend on the timing of the BG readings, and therefore are stationary. In order to capture the dynamics of BG change, measures of the BG rate of change are introduced as provided below.

Computation of BG Risk Rate of Change

Let $x_1, x_2, \ldots x_n$ be n SMBG readings of a subject recorded at time points $t_1, t_2, \ldots t_n$. This data is next transformed by calculating the numbers $f(x_1), f(x_2), \ldots, f(x_n)$ and draw a cubic spline S(t) passing through the points $(t_1, f(x_1)), (t_2, f(x_2)), \ldots, (t_n, f(x_n))$. Thus, the function S(t) is a continuous function defined on the whole interval $[t_1, t_n]$ and such that $S(t_j) = f(x_j)$, for $j=1, \ldots, n$. Also calculated are the set of numbers $s_k = 10 \cdot S(k+t_1)^2$ for $k=0, 1, \ldots, t_n-t_1$ thus getting interpolated values at one-hour increments.

Next, consider all couples of numbers $s_k$ with consecutive indices: $C_0=(s_0,s_1), C_1=(s_1,s_2), C_2=(s_2,s_3), \ldots$ and denote by $M_{up}$ the set of all couples $C_k$, such that $s_k > s_{k+1}$ and by $M_{dn}$ the set of all couples $C_k$, such that $s_k < s_{k+1}$.

Finally, let DrDn be the average of the numbers $s_{k+1}-s_k$, provided that $C_k \in M_{dn}$, and Dr be the average of the numbers $s_{k+1}-s_k$, provided that $C_k \in M_{up}+M_{dn}$.

The numbers DrDn and Dr provide a measure for the rate of change of BG in a "risk space," e.g. the rate of change of the risk associated with any BG level change. In addition, DrDn measures the rate of BG change only when BG goes down, i.e. DrDn evaluates how quickly the risk could increase when BG falls, while Dr is a measure of the overall vulnerability of BG to fluctuations. It is further asserted that DrDn will be associated with risk for hypoglycemia (if someone's blood glucose could fall quickly, his/her risk for hypoglycemia would be higher), while Dr will be associated with the overall stability of BG.

Software Code

Presented in SPSS Control Language

The first is for when the BG readings are in mmol/L, and in this case the variable is BGMM. The second is for when the BG readings are in mg/dl, and in this case the variable is BGMG.

If BG is measured in mmol/L, each BG reading is first transformed as follows:

SCALE1=(ln(BGMM))**1.026−1.861

RISK1=32.185*SCALE1*SCALE1

If BG is measured in mg/dl, each BG reading is first transformed as follows:

SCALE2=(ln(BGMG))**1.08405−5.381

RISK2=22.765*SCALE2*SCALE2

Further, the left and right weighted deviations are computed as follows:

WL=0WL=0

IF (SCALE1 le 0.0) WL=RISK1

WR=0

IF (SCALE1 gt 0.0) WR=sqrt(RISK1)

Provided that the BG readings are equally spaced in time, or are interpolated at one-hour increments, the BG rate of change is computed as:

Dr=RISK1(BG)−RISK1(BG−1)

DrDn=0

IF(SCALE le 0.0 and Dr gt 0) DrDn=Dr

Finally, an aggregation pass through all BG readings for a subject will produce:

WL=mean(WL)

WR=mean(WH)

Dr=mean(Dr), and DrDn=mean(DrDn)

Method for the Evaluation of $HbA_{1c}$

A preferred embodiment of $HbA_{1c}$ evaluation method 100 according to the invention is illustrated in FIG. 1. In a first step 102, SMBG data is collected over a predetermined period of time. For example, the SMBG data is collected over 4-6 weeks with a frequency of 3-5 BG measurements per day, of which are transformed by the code or formulas presented in the previous section. Different formulas are to be used if the BG measurements are stored in mg/dl, or in mmol/l. One skilled in the art would appreciate that various levels, durations, and frequencies can be employed. In a step 104, weighted deviation towards high blood glucose (WR) and estimated rate of change of blood glucose (Dr) is computed using the formula/code discussed above. In a step 106, an estimate of $HbA_{1c}$ from self-monitoring data is computed using the linear function: EstHBA1c=0.9008*WR−0.8207*DR+6.7489. It is noted that the coefficients of this function are derived from data for 867 individuals with diabetes, and one would recognize that further data accumulation may update these coefficients. In step 108 $HbA_{1c}$ estimate categories representing a range of values for estimated $HbA_{1c}$ are defined according to Table 1.

TABLE 1

Defining categories on the basis of EstHBA1c:

| | EstHBA1c | | | | | | |
|---|---|---|---|---|---|---|---|
| | <7.8 | 7.8-8.5 | 8.5-9.0 | 9.0-9.6 | 9.6-10.3 | 10.3-11.0 | >11.0 |
| Category | 1 | 2 | 3 | 4 | 5 | 6 | 7 |

In step 110 predicted confidence intervals for corresponding $HbA_{1c}$ are derived according to Table 2.

TABLE 2

Predicted 95% confidence intervals for classification of $HbA_{1c}$:

| | Category | | | | | | |
|---|---|---|---|---|---|---|---|
| | 1 | 2 | 3 | 4 | 5 | 6 | 7 |
| $HBA_{1c}$ | <8.0 | 8.0-8.5 | 8.5-9.0 | 9.0-9.5 | 9.5-10.1 | 10.1-11.0 | >11.0 |

In step 112, the estimated HbA$_{1c}$ from step 106 is assigned in one of the categories provided in Table 1 and/or Table 2.

Empirical Validation of Evaluation of HbA$_{1c}$

The intervals for HbA$_{1c}$ in Table 2 are based on extensive research. To validate these intervals we analyzed SMBG and HbA$_{1c}$ data from 867 subjects with diabetes. All subjects were instructed to use BG memory meters for six months and to measure their BG two to four times a day. During the same period 5 to 8 HbA$_{1c}$ assays were performed for each subject. The memory meter data were electronically downloaded and stored in a computer for further analysis. This procedure produced a database containing more than 300,000 SMBG readings and 4,180 HbA$_{1c}$ assays taken over six months. Analysis of variance was conducted to compare HbA$_{1c}$ in the seven categories identified in Table 1. The five categories were highly significantly different, with F=91 and p<0.00001. Moreover, the average HbA$_{1c}$ was significantly different for each pair of categories as demonstrated by Duncan's ranges, with p<0.01.

Also, 95% confidence intervals were computed for the mean value of HbA$_{1c}$ in each of the seven categories. These confidence intervals were used as a basis for computing the HbA$_{1c}$ intervals presented in Table 2. Post-hoc analysis of the classification power of this method demonstrated that the method was well protected against extreme errors such as incorrectly classifying HbA$_{1c}$ in category 1, 2 or 3 on the basis of SMBG while the actual HbA$_{1c}$ was greater than 9.5%, or classifying HbA$_{1c}$ in category 5, 6 or 7 while the actual HbA$_{1c}$ was below 9.0%.

In summary, after an initial 4-6 weeks of SMBG readings the computerized method computes an interval estimate for the value of HbA$_{1c}$ that can be used to track patients' changes in glycemic control in the high BG range.

Method for Evaluation of the Long-Term Probability for Severe Hypoglycemia (SH)

Figure 2:
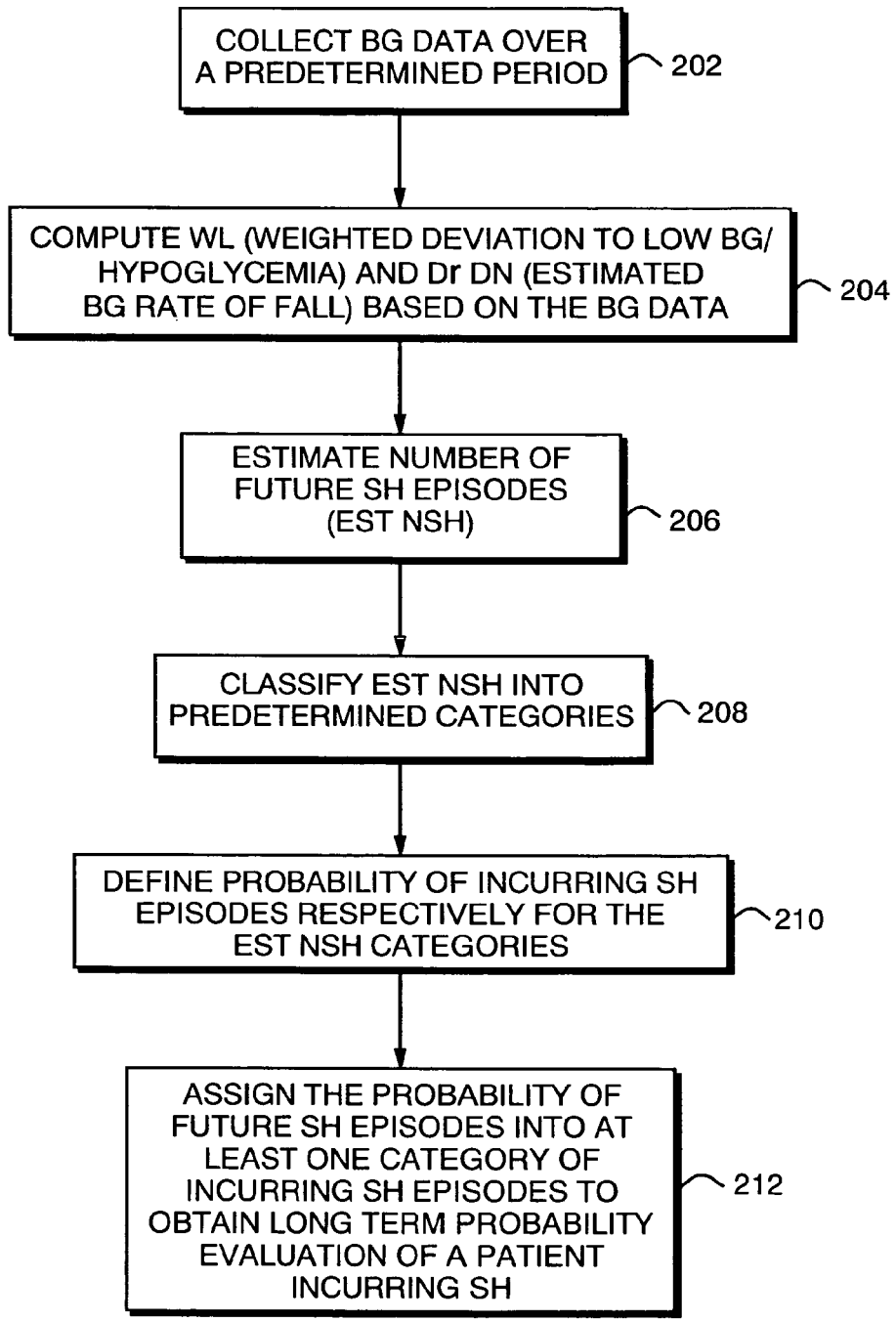
FIG. 2 is a flow chart illustrating the method of calculating the estimated number of future SH episodes and the associated probability thereof in accordance with the present invention.

A preferred embodiment of long-term probability for SH evaluation method 200 according to the invention is illustrated in FIG. 2. In a first step 202, SMBG data is collected over a predetermined period of time. For example, the SMBG data is collected over 4-6 weeks with a frequency of 3-5 BG measurements per day, of which are transformed by the code or formulas presented immediately above. Different formulas are to be used if the BG measurements are stored in mg/dl, or in mmol/l; One skilled in the art would appreciate that various levels, durations, and frequencies can be employed. In a step 204, WL and DrDn are computed using the formula/code as discussed above. In step 206, an estimate of the number of future SH episodes is computed using the linear function:

$$EstNSH = 3.3613 * WL - 4.3427 * DrDn - 1.2716.$$

It is noted that the coefficients of this function are derived from data for 181 individuals with diabetes, and one would appreciate that further data accumulation may update these coefficients. It is further noted that this formula provides a single value estimate for the number of future SH episodes and that through additional methodologies, as discussed below, categories are provided with ranges and confidence levels for enhanced clinical applications. In step 208, estimated number of SH episodes (estNSH) categories representing a range of values for estNSH are defined according to Table 3.

TABLE 3

Classification of EstNSH:

| | EstNSH | | | |
|---|---|---|---|---|
| | <0.775 | 0.775-3.750 | 3.750-7.000 | >7.000 |
| Category | 1 | 2 | 3 | 4 |

In step 210, respective to the estNSH categories, the probability of incurring 0, 1-2, or more than 2 SH episodes in the following six months is derived, as represented in table 4.

TABLE 4

Probability for 0, 1-2, or 2 or more
SH episodes in the subsequent 6 months:

| | Category 1 | Category 2 | Category 3 | Category 4 |
|---|---|---|---|---|
| 0 SH | 90% | 50% | 25% | <20% |
| 1-2 SH | 10% | 25% | 25% | |
| >2 SH | | 25% | 50% | >80% |

In step 212, the EstNSH from step 206 is assigned in one of the categories provided in Table 3 and/or Table 4.

Empirical Validation of Evaluation of the Long-Term Probability for SH

One-hundred-eighty-one adults with Type 1 diabetes (mean age 37 years, duration of diabetes 18 years) used memory meters to collect more than 34,000 SMBG over a month. Then for the next six months they recorded in diaries any occurrence of SH. The SMBG data were mathematically transformed and an a linear regression model was used to predict future severe hypoglycemia resulting in a highly significant model (F=36.3, p<0.0001) and multiple R of 55%.

All subjects were classified into 4 categories using the present long-term SH method. The average number of future SH episodes in categories 1, 2, 3, and 4 was 0.3, 2.0, 5.0, and 9.75 respectively. Analysis of variance demonstrated highly significant differences between these categories, F=19.0, p<0.0001.

In summary, a linear combination of the Low BG Index and the rate of drop of BG as measured in "risk space" provide an accurate assessment of the long-term risk of SH. Because it is based on SMBG records that are automatically stored by many reflectance meters, this is an effective and clinically useful indicator of patients' glycemic control in the low BG range.

Figure 3:
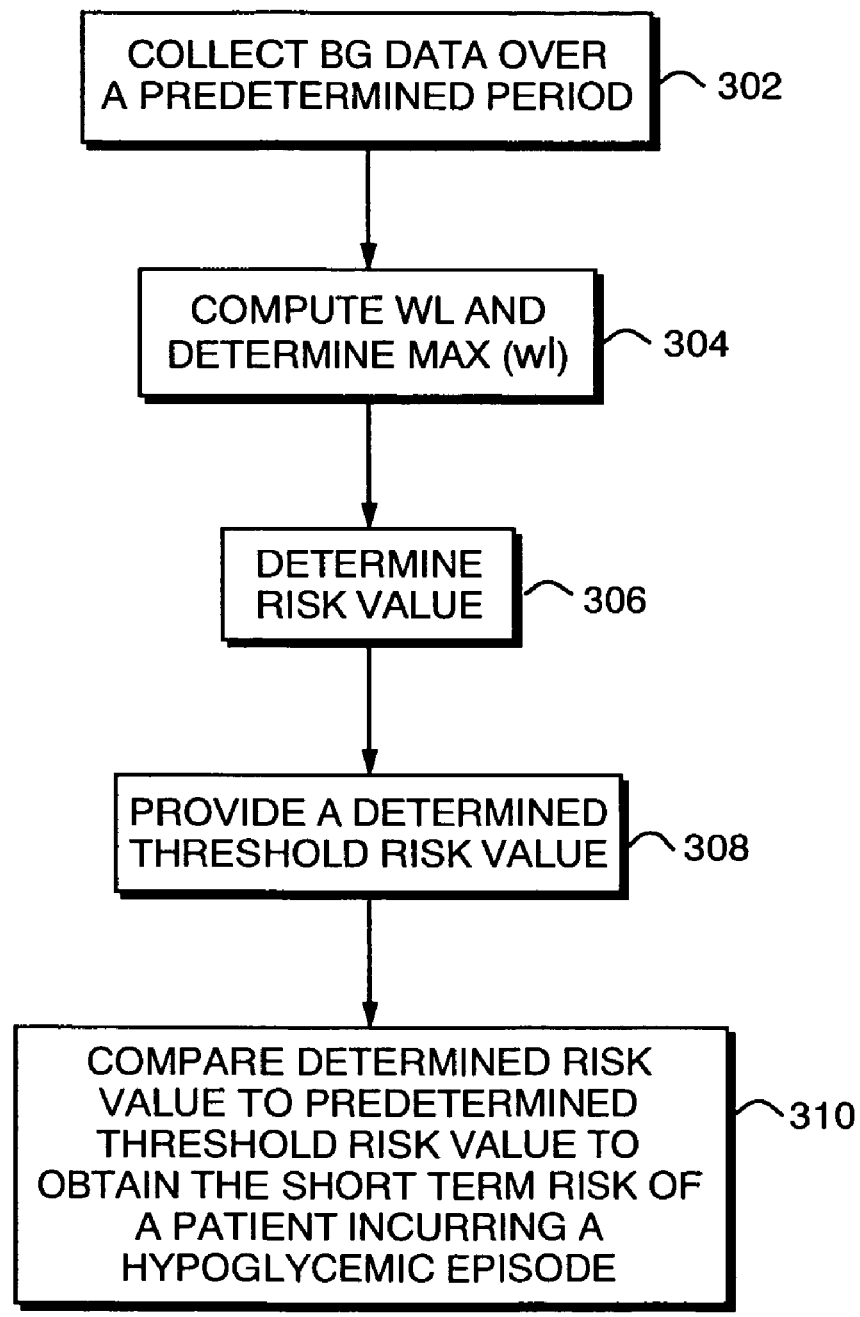
FIG. 3 is a flow chart illustrating the method of calculating the estimated short term risk of an incurring imminent SH in accordance with the present invention.

Method for the Evaluation of the Short-Term (within 24 hours) Risk of Hypoglycemia A preferred embodiment of short term risk of SH evaluation method 300 according to the invention is illustrated in FIG. 3. In a first step 302, SMBG is data is collected over a predetermined short term period. For example, the SMBG data is collected over a 24 hour period, with a frequency of 3-5 BG measurements per day –4 or more readings, as a nominal level according to data analyses. One skilled in the art would appreciate that various levels, periods (durations), and frequencies can be employed. In a step 304 WL(24) and Max (wl) is computed from all readings collected within the preceding 24 hours, wherein the maximum value of wl(BG;2) is Max(wl). In step 306, the risk value is by taking the geometric mean of WL and Max(wl) over the 24 hour period, wherein said risk value is mathematically defined as:

$$Risk(24) = \sqrt{WL(24) \cdot Max(wl)};$$

In step 308 a threshold risk value is determined. In step 310 the estimated risk value is compared to the threshold risk value. For example, if the threshold risk value is set at 17, then if Risk(24)>17, then—based on the SMBG data collected over the previous 24 hours—the resultant indication is a high risk of the patient incurring imminent hypoglycemia. In other words, this is a decision-making rule that considers a 24-hour period of SMBG data and judges whether this period is likely to precede an imminent hypoglycemia episode. The threshold value of 17 is derived from an extensive data set, however, it is recognized that it is possible that this value maybe adjusted with further accumulation of data or for additional objectives.

Empirical Validation of Evaluation of the Short-Term Risk of Hypoglycemia

Eighty-five individuals were recruited through advertisement in newsletters, diabetes clinics, and through direct referrals. The inclusion criteria were: 1) age of 21-60 years; 2) type I diabetes with at least two years duration, and insulin use since the time of diagnosis; 3) at least 2 documented SH episodes in the past year; and 4) routine use of SMBG devices for diabetes monitoring. The participants were instructed to use the meter 3-5 times a day, and to record in monthly diaries any SH episodes, including the exact dates and times of their occurrences. SH was defined as severe neuroglycopenia that results in stupor or unconsciousness and precludes self-treatment. For each subject the study continued 6-8 months and each month the subject's meter was downloaded and the SH diary was collected. The memory capacity of the meters was sufficient, and the downloading was often enough, so that no BG data were lost. No changes were made in the participants' diabetes management routine, nor were any additional treatments administered during the study.

During the study a total of 75,495 SMBG readings (on average $4.0 \pm 1.5$ per subject per day) were downloaded from the participants' memory meters, and 399 ($4.7 \pm 6.0$ per subject) SH episodes were recorded in their diaries. An important finding, among other things, was that episodes of moderate or severe hypoglycemia are preceded and followed by measurable BG disturbances. In the 24-hour period before an SH episode the Low BG Index (e.g. WL) rose ($p<0.001$), the average BG was lower ($p=0.001$), and the BG variance increased ($p=0.001$). In the 24 hours following the SH episode, the Low BG Index and BG variance remained elevated ($p<0.001$), but the average BG returned to its baseline.

Figure 4:
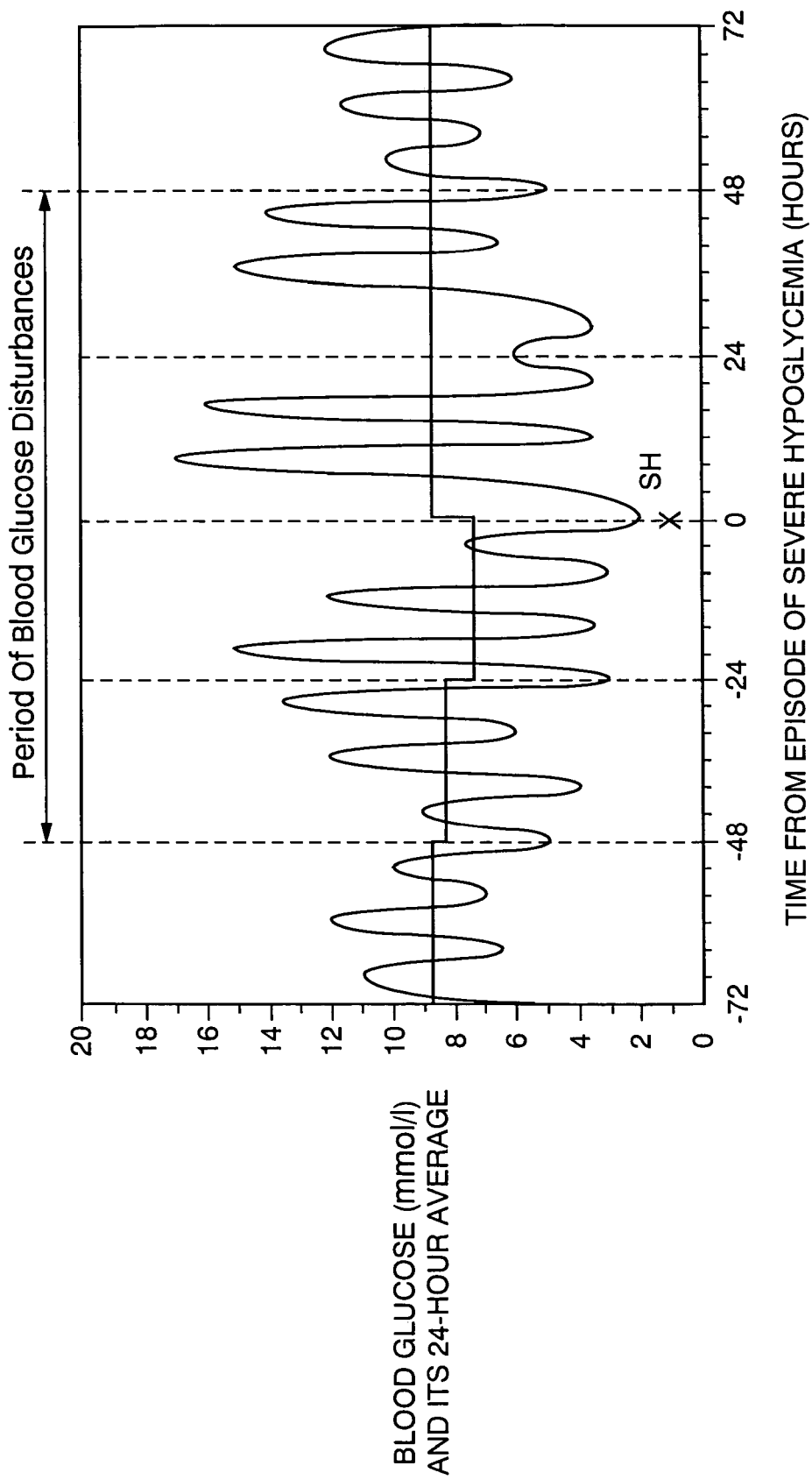
FIG. 4 is graphical representation of a typical BG disturbances observed before and after an episode of severe hypoglycemia.

To this end, FIG. 4 is graphical representation of a typical BG disturbance observed before and after an episode of severe hypoglycemia. In the period 48 to 24 hours before the SH episode, the average BG level decreased and the variance of BG increased. In the 24-hour period immediately preceding the SH episode, the average BG level dropped further and the variance of BG continued to increase. In the 24-hour period following the SH episode, the average BG level normalized, but the BG variance remained greatly increased. Both the average BG and its variance returned to their baseline levels within 48 hours after the SH episode.

As such, as part of the invention, the disturbances presented in FIG. 4 are quantified from SMBG data to enable the evaluation of the short-term risk of hypoglycemia. The cutoff value of Risk(24)=17 is derived from an optimization along the following restrictions: 1) the method had to predict a maximum percentage of SH episodes, i.e. to identify as risky a maximum percentage of 24-hour periods preceding SH, and 2) to prevent overestimation of the risk, the method had to identify as risky no more that 15% of the total time of the study (one day a week on average). The cutoff risk value of 17 was held constant for all subjects. The reason for choosing the value of 15% was to prevent the patients from becoming irritated with an overabundance of "false alarms" and then ignoring "true alarms." In practice, a patient's physician can select an alternate value depending on the severity of the patient's diabetes and particular objectives.

Figure 5:
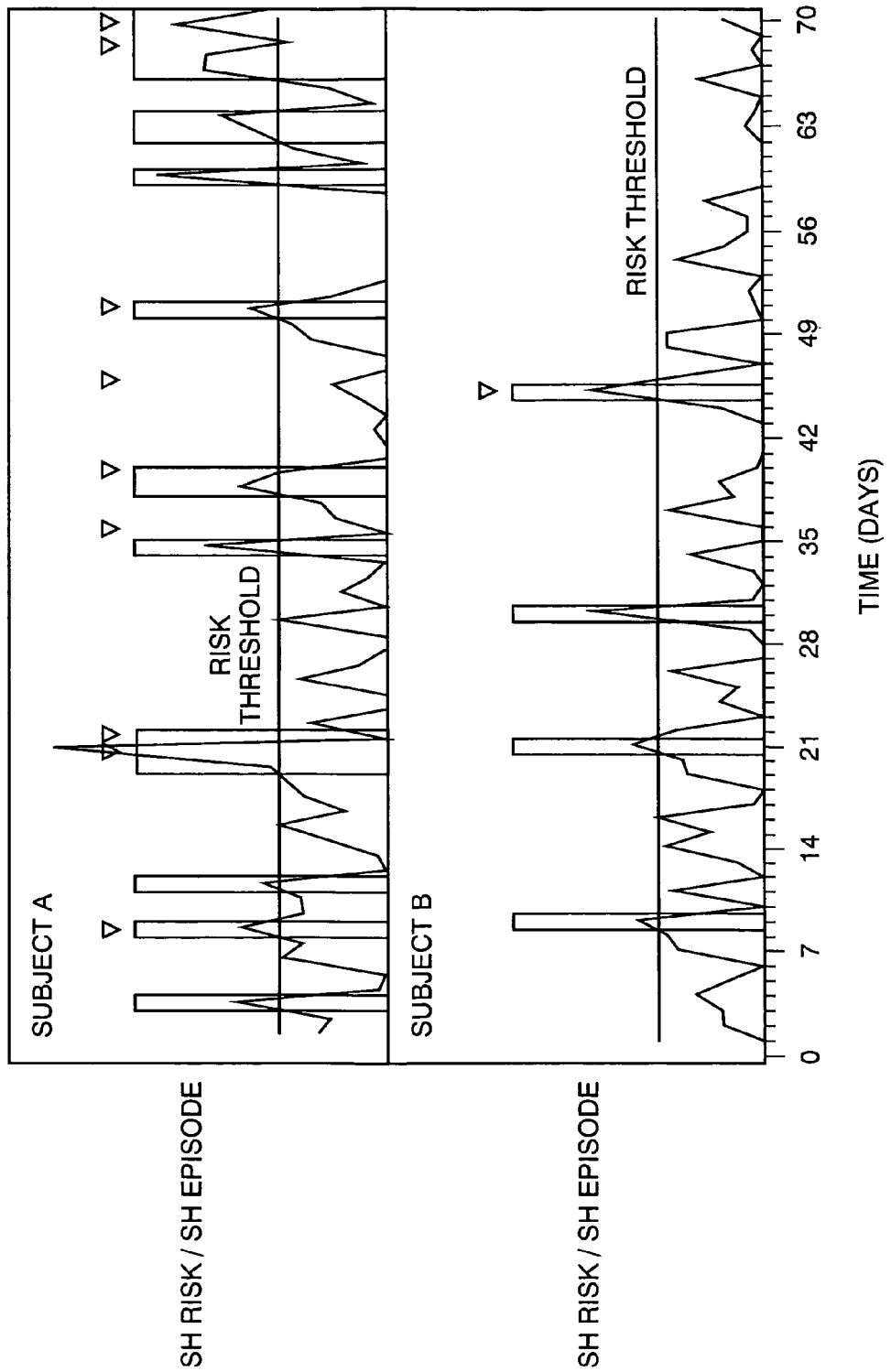
FIG. 5 illustrates action of the method for predicting short-term SH by presenting 10 weeks of data for Subject A (upper panel) and Subject B (lower panel). SH episodes are marked by triangle; a black line presents the risk value. When the risk threshold is crossed, the method indicates a subsequent high-risk period (gray bar).

The following example illustrates the action of the algorithm on the SMBG data of two participants in the study. FIG. 5 presents ten weeks of data for Subject A (upper panel) and Subject B (lower panel). SH episodes are marked by triangles; a black curve presents the risk value. When the risk threshold (the horizontal line at Risk=17) is crossed, the algorithm indicates a subsequent high-risk period (gray bar). For Subject A, 7 out of 9 SH episodes are predicted and there are 5 false alarms, e.g. high-risk periods that did not result in SH; for Subject B there are 3 false alarms and the only SH episode is predicted. It is obvious that Subject B's risk values when compared to Subject A's risk values, include more and higher deviations. For both subjects, all SH episodes were accompanied by supercritical risk values, and about half of all large deviations were accompanied by one or more SH episode.

Across all participants in the study, 44% of all recorded SH episodes were preceded, within 24 hours, by a high-risk period, and 50% were preceded, within 48 hours, by a high-risk period. If only periods with either at least 3, or at least 4 SMBG measurements were considered, the accuracy of the latter prediction increased to 53% and 57%, respectively. Post-hoc analysis of BG levels occurring during, or immediately after, high-risk periods that were not followed by an SH episode, i.e. during, or immediately after false alarms, demonstrated that the average per subject minimum of such BG levels was $2.3 \pm 0.2$ mmol/l versus $5.9 \pm 1.7$ mmol/l ($t=19.5$, $p<0.0001$) for all non-risk periods, including all SH episodes that remained unaccounted for. This indicates that, although symptomatic SH did not occur, BG levels following high-risk periods were notably low.

In summary, the inventors simulated the action of the short-term risk method on a 6-month series of SMBG readings for 85 individuals with Type I diabetes. With four or more SMBG readings per day, at least 50% of all episodes of SH could be anticipated. Even when symptomatic SH did not occur, the algorithm predicted episodes of moderate hypoglycemia.

Integration of the Three Methods

The three methods of this invention, as discussed above and illustrated in FIGS. 1-3, utilize the same series of SMBG data. Therefore, from an SMBG-device point of view, a unified display or matrix of the results of these three methods could be made similar to the grid output presented below:

|  |  | EstHBA categories (Algorithm 1) | | | | | | |
|---|---|---|---|---|---|---|---|---|
|  |  | 1 | 2 | 3 | 4 | 5 | 6 | 7 |
| EstNSH categories | 1 |  |  |  | Ss 1 |  |  |  |
|  | 2 |  |  |  |  |  |  |  |
|  | 3 |  |  |  |  |  |  |  |
|  | 4 |  | Ss 2 |  |  |  |  |  |

Thus, for example, the output for subject 1 (Ss 1) shown in the above grid indicates that this person is likely to have HbA$_{1c}$ between 9 and 9.5%, and has a 90% chance not to experience severe hypoglycemia in the subsequent 6 months. The output for subject 2 (Ss 2) indicates that this person is likely to have HbA$_{1c}$ below 8%, and has a greater than 80% chance to experience at least 3 SH episodes in the subsequent 6 months.

In addition to this grid-output, the short term risk method provides a continuous tracking of the risk of imminent hypoglycemia and can be used to sound an alarm when this risk becomes high.

Figure 6:
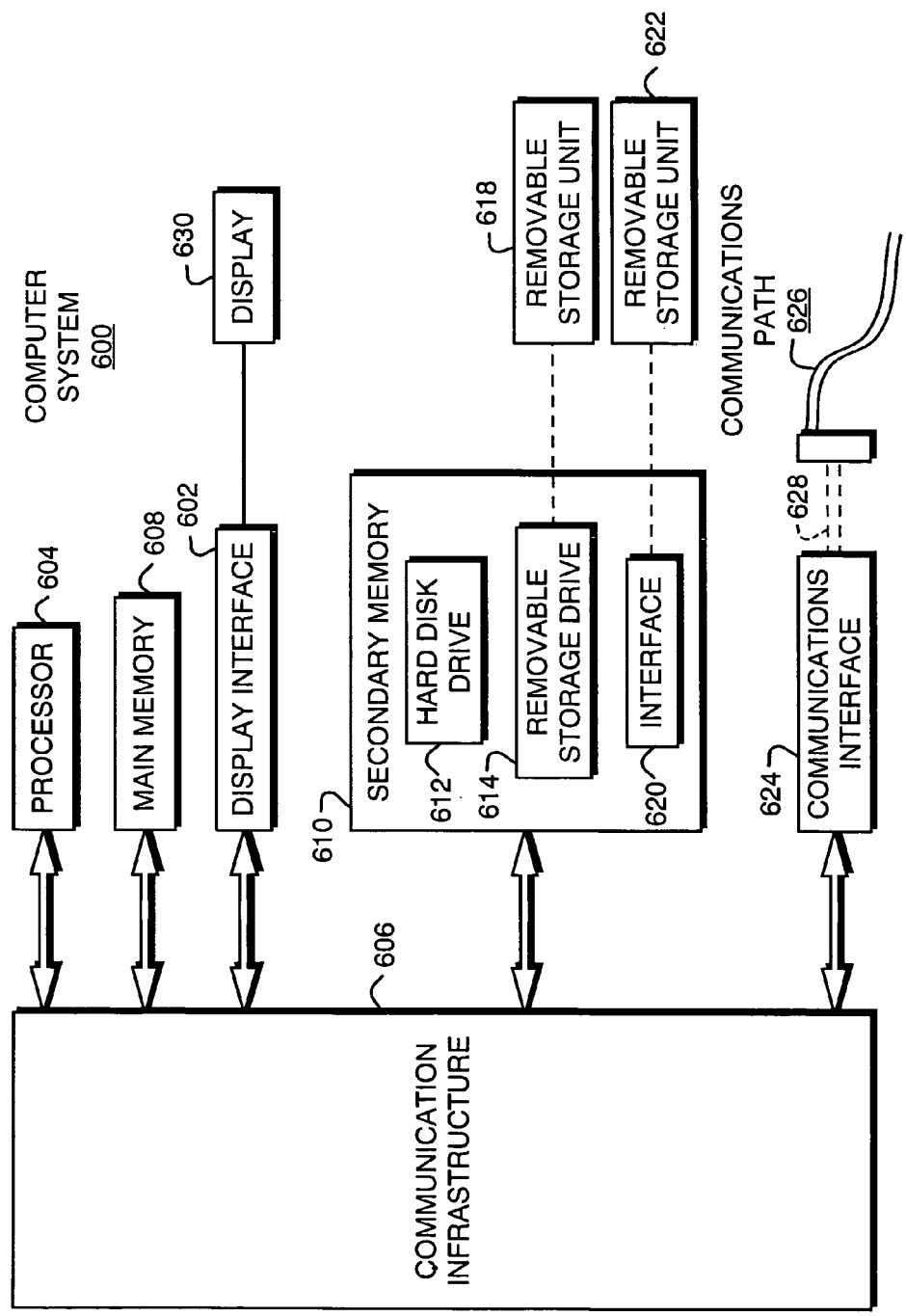
FIG. 6 is a functional block diagram for a computer system for implementation of the present invention.

The method of the invention may be implemented using hardware, software or a combination thereof and may be implemented in one or more computer systems or other processing systems, such as personal digit assistants (PDAs). In an example embodiment, the invention was implemented in software running on a general purpose computer 900 as illustrated in FIG. 6. Computer system 600 includes one or more processors, such as processor 604. Processor 604 is connected to a communication infrastructure 606 (e.g., a communications bus, cross-over bar, or network). Computer system 600 includes a display interface 602 that forwards graphics, text, and other data from the communication infrastructure 606 (or from a frame buffer not shown) for display on the display unit 630.

Computer system 600 also includes a main memory 608, preferably random access memory (RAM), and may also include a secondary memory 610. The secondary memory 610 may include, for example, a hard disk drive 612 and/or a removable storage drive 614, representing a floppy disk drive, a magnetic tape drive, an optical disk drive, etc. The removable storage drive 614 reads from and/or writes to a removable storage unit 618 in a well known manner. Removable storage unit 618, represents a floppy disk, magnetic tape, optical disk, etc. which is read by and written to by removable storage drive 614. As will be appreciated, the removable storage unit 618 includes a computer usable storage medium having stored therein computer software and/or data.

In alternative embodiments, secondary memory 610 may include other means for allowing computer programs or other instructions to be loaded into computer system 600. Such means may include, for example, a removable storage unit 622 and an interface 620. Examples of such removable storage units/interfaces include a program cartridge and cartridge interface (such as that found in video game devices), a removable memory chip (such as a ROM, PROM, EPROM or EEPROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between computer system 600 and external devices. Examples of communications interface 624 may include a modem, a network interface (such as an Ethernet card), a communications port, a PCMCIA slot and card, etc. Software and data transferred via communications interface 624 are in the form of signals 628 which may be electronic, electromagnetic, optical or other signals capable of being received by communications interface 624. Signals 628 are provided to communications interface 624 via a communications path (i.e., channel) 626. Channel 626 carries signals 628 and may be implemented using wire or cable, fiber optics, a phone line, a cellular phone link, an RF link and other communications channels.

In this document, the terms "computer program medium" and "computer usable medium" are used to generally refer to media such as removable storage drive 914, a hard disk installed in hard disk drive 612, and signals 628. These computer program products are means for providing software to computer system 600. The invention includes such computer program products.

Computer programs (also called computer control logic) are stored in main memory 608 and/or secondary memory 610. Computer programs may also be received via communications interface 624. Such computer programs, when executed, enable computer system 600 to perform the features of the present invention as discussed herein. In particular, the computer programs, when executed, enable processor 604 to perform the functions of the present invention. Accordingly, such computer programs represent controllers of computer system 600.

In an embodiment where the invention is implemented using software, the software may be stored in a computer program product and loaded into computer system 600 using removable storage drive 614, hard drive 612 or communications interface 624. The control logic (software), when executed by the processor 604, causes the processor 604 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above were implemented in SPSS control language, but could be implemented in other programs such as, but not limited to, C++ programming language.

Figure 7:
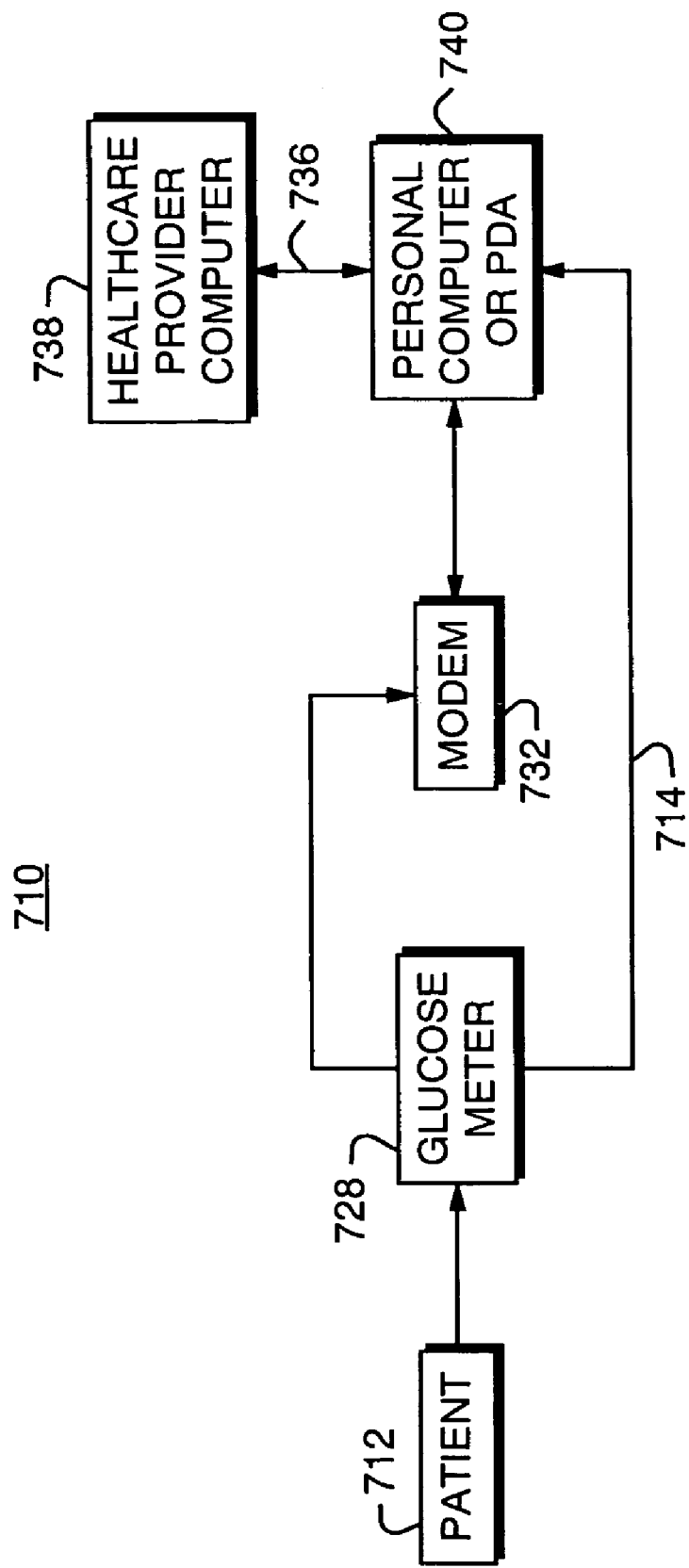
FIGS. 7-9 are schematic block diagrams of alternative variations of the present invention related processors, communication links, and systems.
Figure 8:
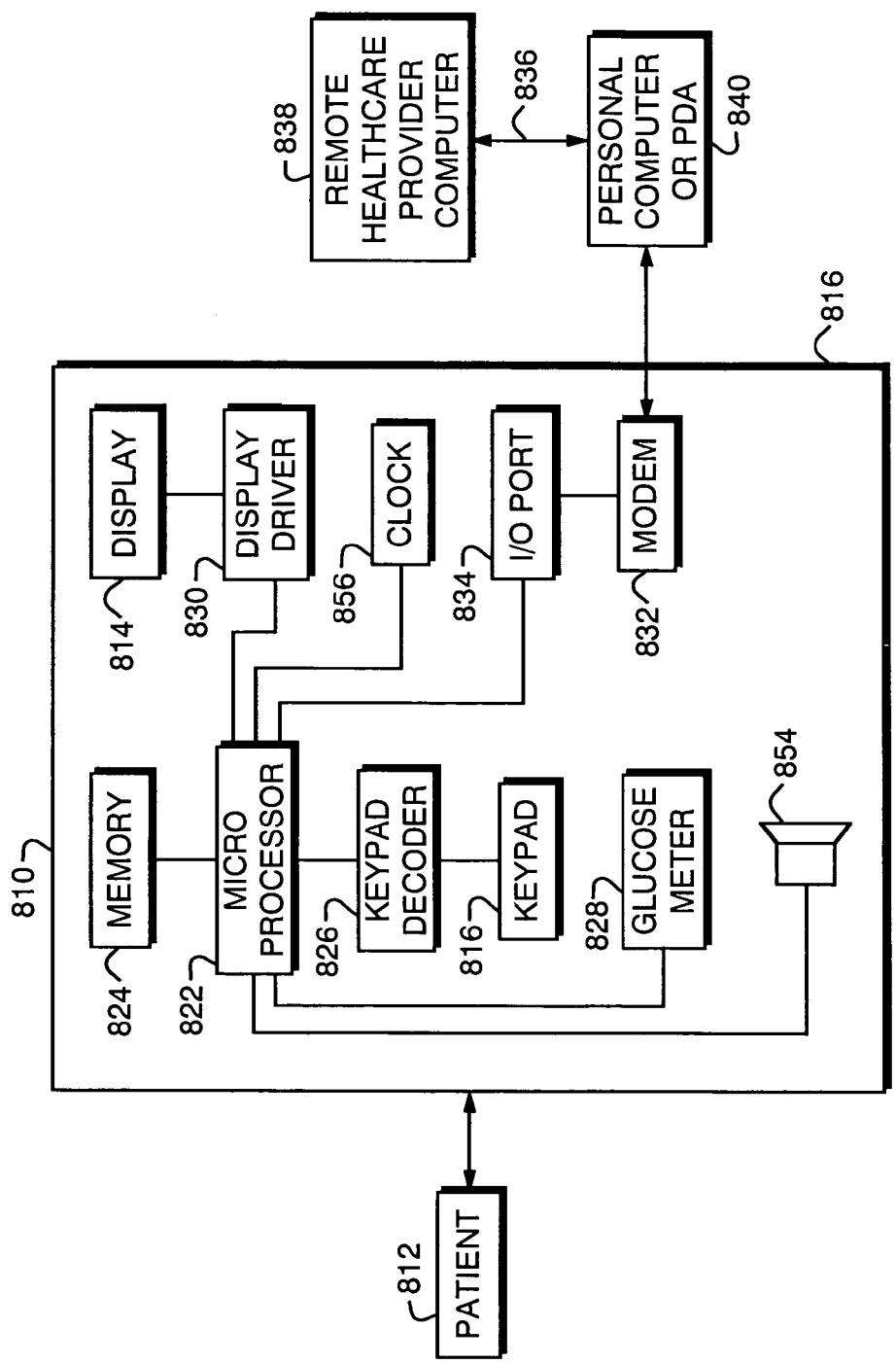
Figure 9:
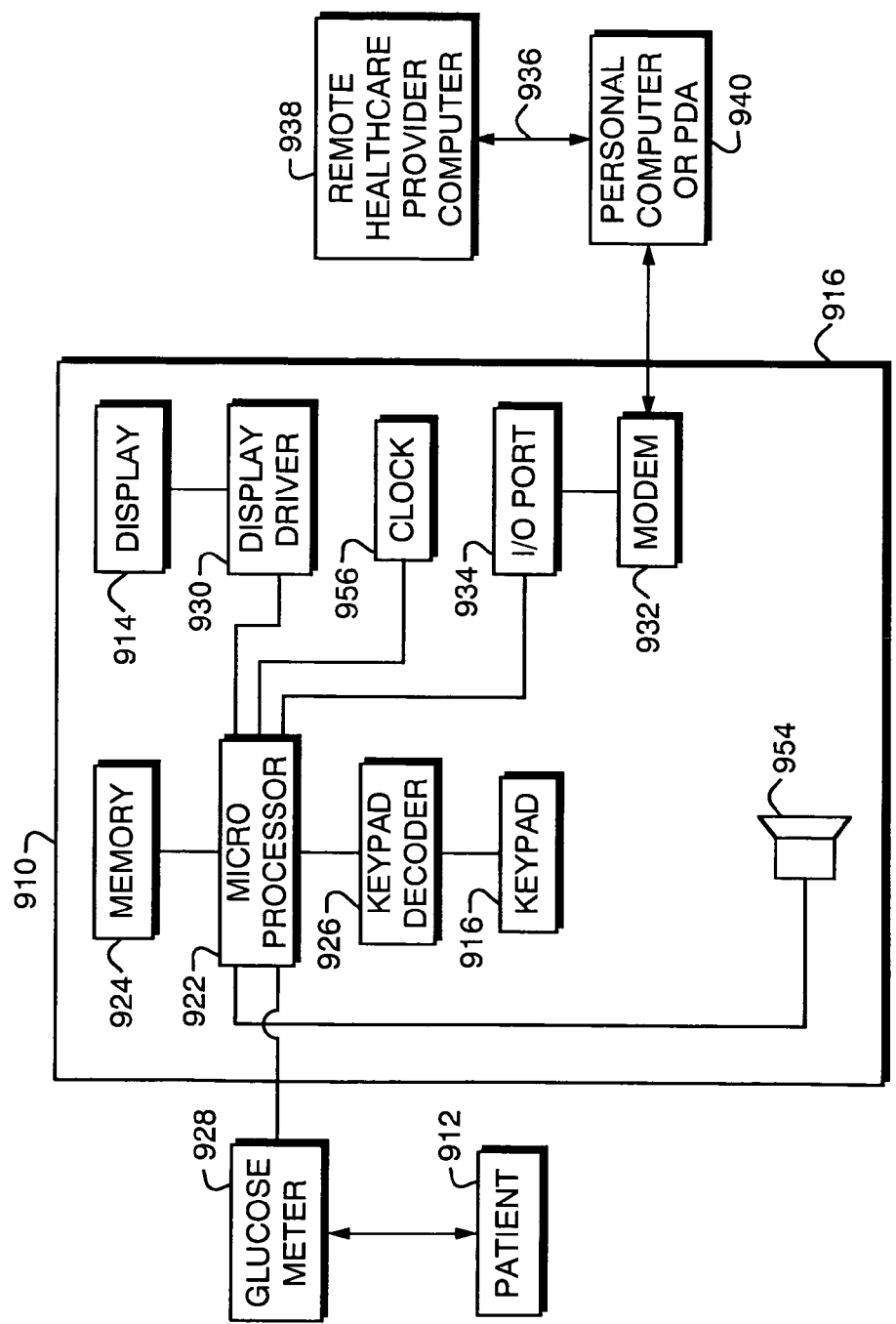

FIGS. 7-9 show block diagrammatic representation of alternative embodiments of the invention. Referring FIG. 7, there is shown a block diagrammatic representation of the system 710 essentially comprises the glucose meter 728 used by a patient 712 for recording, inter alia, insulin dosage readings and measured blood glucose ("BG") levels, Data obtained by the glucose meter 728 is preferably transferred through appropriate communication links 714 or data modem 732 to a processing station or chip, such as a personal computer 740, PDA, or cellular telephone. For instance, data stored may be stored within the glucose meter 728 and may be directly downloaded into the personal computer 740 through an appropriate interface cable. An example is the ONE TOUCH monitoring system or meter by LifeScan, Inc. which is compatible with IN TOUCH software which includes an interface cable to down load the data to a personal computer.

The glucose meter is common in the industry and includes essentially any device that can functions as a BG acquisition mechanism. The BG meter or acquisition mechanism, device, tool, or system includes various conventional methods directed toward drawing a blood sample (e.g. by fingerprick) for each test, and a determination of the glucose level using an instrument that reads glucose concentrations by electromechanical or claorimetric methods. Recently, various methods for determining the concentration of blood analytes without drawing blood have been developed. For example, U.S. Pat. No. 5,267,152 to Yang et al. describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al.

U.S. Pat. No. 5,139,023 to Stanley describes a transdermal blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder.

In addition, U.S. Pat. No. 5,279,543 to Glikfeld describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose. Moreover, International Publication No. WO 96/00110 to Tamada describes an iontophoretic apparatus for transdermal monitoring of a target substance, wherein an iontophoretic electrode is used to move an analyte into a collection reservoir and a biosensor is used to detect the target analyte present in the reservoir. Finally, U.S. Pat. No. 6,144,869 to Berner describes a sampling system for measuring the concentration of an analyte present.

Further yet, the BG meter or acquisition mechanism may include indwelling catheters and subcutaneous tissue fluid sampling.

The computer or PDA 740 includes the software and hardware necessary to process, analyze and interpret the self-recorded diabetes patient data in accordance with predefined flow sequences (as described above in detail) and generate an appropriate data interpretation output. Preferably, the results of the data analysis and interpretation performed upon the stored patient data by the computer 740 are displayed in the form of a paper report generated through a printer associated with the personal computer 740. Alternatively, the results of the data interpretation procedure may be directly displayed on a video display unit associated with the computer 740.

FIG. 8 shows a block diagrammatic representation of an alternative embodiment having a diabetes management system that is a patient-operated apparatus 810 having a housing preferably sufficiently compact to enable apparatus 810 to be hand-held and carried by a patient. A strip guide for receiving a blood glucose test strip (not shown) is located on a surface of housing 816. Test strip is for receiving a blood sample from the patient 812. The apparatus includes a microprocessor 822 and a memory 824 connected to microprocessor 822. Microprocessor 22 is designed to execute a computer program stored in memory 824 to perform the various calculations and control functions as discussed in great detail above. A keypad 816 is connected to microprocessor 822 through a standard keypad decoder 826. Display 814 is connected to microprocessor 822 through a display driver 830. Microprocessor 822 communicates with display driver 830 via an interface, and display driver 830 updates and refreshes display 814 under the control of microprocessor 822. Speaker 854 and a clock 856 are also connected to microprocessor 822. Speaker 854 operates under the control of microprocessor 822 to emit audible tones alerting the patient to possible future hypoglycemia. Clock 856 supplies the current date and time to microprocessor 822.

Memory 824 also stores blood glucose values of the patient 812, the insulin dose values, the insulin types, and the parameter values used by microprocessor 822 to calculate future blood glucose values, supplemental insulin doses, and carbohydrate supplements. Each blood glucose value and insulin dose value is stored in memory 824 with a corresponding date and time. Memory 824 is preferably a non-volatile memory, such as an electrically erasable read only memory (EEPROM).

Apparatus 810 also includes a blood glucose meter 828 connected to microprocessor 822. Glucose meter 828 is designed to measure blood samples received on blood glucose test strips and to produce blood glucose values from measurements of the blood samples. As mentioned previously, such glucose meters are well known in the art. Glucose meter 828 is preferably of the type which produces digital values which are output directly to microprocessor 822. Alternatively, blood glucose meter 828 may be of the type which produces analog values. In this alternative embodiment, blood glucose meter 828 is connected to microprocessor 822 through an analog to digital converter (not shown).

Apparatus 810 further includes an input/output port 834, preferably a serial port, which is connected to microprocessor 822. Port 834 is connected to a modem 832 by an interface, preferably a standard RS232 interface. Modem 832 is for establishing a communication link between apparatus 810 and a personal computer 840 or a healthcare provider computer 838 through a communication network 836. Specific techniques for connecting electronic devices through connection cords are well known in the art. Another alternative example is "bluetooth" technology communication.

Alternatively, FIG. 9 shows a block diagrammatic representation of an alternative embodiment having a diabetes management system that is a patient-operated apparatus 910, similar as shown in FIG. 8, having a housing preferably sufficiently compact to enable the apparatus 910 to be hand-held and carried by a patient. However, the present embodiment includes a separate or detachable glucose meter or BG acquisition mechanism 928.

Accordingly, the embodiments described herein are capable of being implemented over data communication networks such as the internet, making evaluations, estimates, and information accessible to any processor or computer at any remote location, as depicted in FIGS. 6-9 and/or U.S. Pat. No. 5,851,186 to Wood, of which is hereby incorporated by reference herein. Alternatively, patients located at remote locations may have the BG data transmitted to a central healthcare provider or residence, or a different remote location.

In summary, the invention proposes a data analysis computerized method and system for the simultaneous evaluation of the two most important components of glycemic control in individuals with diabetes: $HbA_{1c}$ and the risk of hypoglycemia. The method, while using only routine SMBG data, provides, among other things, three sets of output.

The potential implementations of the method, system, and computer program product of the invention is that it provides the following advantages, but are not limited thereto. First, the invention enhances existing home BG monitoring devices by producing and displaying: 1) estimated categories for $HbA_{1c}$, 2) estimated probability for SH in the subsequent six months, and 3) estimated short-term risk of hypoglycemia (i.e. for the next 24 hours). The latter may include warnings, such as an alarm, that indicates imminent hypoglycemic episodes. These three components can also be integrated to provide continuous information about the glycemic control of individuals with diabetes, and to enhance the monitoring of their risk of hypoglycemia.

As a second advantage, the invention enhances existing software or hardware that retrieves SMBG data. Such software or hardware is produced by virtually every manufacturer of home BG monitoring devices and is customarily used by patients and health care providers to interpret SMBG data. The methods and system of the invention can be directly incorporated into existing home blood glucose monitors, or used for the enhancement of software that retrieves SMBG data, by introducing a data interpretation component capable of predicting both $HbA_{1c}$ and periods of increased risk of hypoglycemia.

Still yet another advantage, the invention evaluates the accuracy of home BG monitoring devices, both in the low and high BG ranges, and over the entire BG scale.

Moreover, another advantage, the invention evaluates the effectiveness of various treatments for diabetes.

Further still, as patients with diabetes face a life-long optimization problem of maintaining strict glycemic control without increasing their risk of hypoglycemia, the present invention alleviates this related problem by use of its simple and reliable methods, i.e., the invention is capable of evaluating both patients' glycemic control and their risk of hypoglycemia, and at the same time applying it in their everyday environments.

Additionally, the invention provides the missing link by proposing three distinct, but compatible, algorithms for evaluating $HbA_{1c}$ and the risk of hypoglycemia from SMBG data, to be used to predict the short-term and long-term risks of hypoglycemia, and the long-term risk of hyperglycemia.

Finally, another advantage, the invention evaluates the effectiveness of new insulin or insulin delivery devices. Any manufacturer or researcher of insulin or insulin delivery devices can utilize the embodiments of the invention to test the relative success of proposed or tested insulin types or device delivery designs.

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes which come within the meaning and range of equivalency of the claims are therefore intended to be embraced therein.

We claim:

1. A computerized method for evaluating hemoglobin $A_{1c}$ ($HbA_{1c}$) of a patient based on blood glucose (BG) data collected over a predetermined duration, said method comprising:

computing on a computer weighted deviation of the BG of said patient toward high blood glucose (WR) from a predefined normal level;

computing on a computer mean blood glucose (Dr); and estimating on a computer $HbA_{1c}$ using a predetermined mathematical formula based on said computed WR and Dr;

defining predetermined categories for the estimate of $HbA_{1c}$, each of said $HbA_{1c}$ estimate categories representing a range of values for estimated $HbA_{1c}$; and assigning said estimated $HbA_{1c}$ to at least one of said $HbA_{1c}$ estimate categories.

2. The method of claim 1, wherein:

said computed WR is mathematically defined from a series of BG readings $x_1, x_2, \ldots x_n$ taken at time points $t_1, t_2, \ldots t_n$ as:

$$WR = \frac{1}{n}\sum_{i=1}^{n} wr(x_i, 1)$$

where:

$wr(BG,b) = 10f(BG)^b$ if $f(BG) > 0$ and 0 otherwise, where $f$ is a symmetrization function, $b=1$, representing a weighting parameter, and said computed Dr is mathematically defined as:

$Dr$ = average of $s_{k+1} - s_k$, where:

$s_k = 10S(k+t_1)^2$ for $k=0, 1, \ldots, t_n-t_1$, $S(t_1) = f(x_j)$, for $j=1, \ldots, n$, where $x_j$ is a BG reading of said patient at time $j$.

3. The method of claim 1, wherein said estimating $HbA_{1c}$ from said BG monitoring data comprises determining Estimated $HbA_{1c}$ according to:

Estimated $HbA_{1c} = 0.9008(WR) - 0.8207(DR) + 6.7489$.

4. The method of claim 1, wherein said $HbA_{1c}$ estimate categories are defined as follows:

classified category 1, wherein said estimated $HbA_{1c}$ is less than about 7.8;

classified category 2, wherein said estimated $HbA_{1c}$ is between about 7.8 and about 8.5;

classified category 3, wherein said estimated $HbA_{1c}$ is between about 8.5 and about 9.0;

classified category 4, wherein said estimated $HbA_{1c}$ is between about 9.0 and about 9.6;

classified category 5, wherein said estimated $HbA_{1c}$ is between about 9.6 and about 10.3;

classified category 6, wherein said estimated $HbA_{1c}$ is between about 10.3 and about 11.0; and classified category 7, wherein said estimated $HbA_{1c}$ is above about 11.0.

5. The method of claim 4, further comprising:

defining predicted confidence intervals for corresponding said $HbA_{1c}$ estimate categories, wherein said predicted confidence intervals are defined as follows:

said classified category 1 corresponds with a predicted $HbA_{1c}$ less than about 8.0;

said classified category 2 corresponds with a predicted $HbA_{1c}$ between about 8.0 and about 8.5;

said classified category 3 corresponds with a predicted $HbA_{1c}$ between about 8.5 and about 9.0;

said classified category 4 corresponds with a predicted $HbA_{1c}$ between about 9.0 and about 9.5;

said classified category 5 corresponds with a predicted $HbA_{1c}$ between about 9.5 and about 10.1;

said classified category 6 corresponds with a predicted $HbA_{1c}$ between about 10.1 and about 11.0; and said classified category 7 corresponds with a predicted $HbA_{1c}$ above about 11.0.

6. The method of claim 1, further comprising:

defining predicted confidence intervals for corresponding said $HbA_{1c}$, each of said predicted confidence intervals representing a range of values for $HbA_{1c}$.

7. The method of claim 6, wherein said predicted $HbA_{1c}$ confidence intervals have about a 95% confidence level.

8. A computerized method for evaluating hemoglobin $A_{1c}$ ($HbA_{1c}$) of a patient based on blood glucose (BG) data collected over a predetermined duration, said method comprising:

computing on a computer weighted deviation of the BG of said patient toward high blood glucose (WR) from a predefined normal level;

computing on a computer mean blood glucose (Dr) based on said collected BG data;

estimating on a computer $HbA_{1c}$ using a predetermined mathematical formula based on said computed WR and Dr; and providing on a computer a predetermined confidence interval for classification of said estimated value of $HbA_{1c}$.

9. The method of claim 8, wherein:

said confidence interval is between about 85% to about 95%.

10. The method of claim 8, wherein:

said computed WR is mathematically defined from a series of BG readings $x_1, x_2, \ldots x_n$ taken at time points $t_1, t_2, \ldots, t_n$ as:

$$WR = \frac{1}{n}\sum_{i=1}^{n} wr(x_i, 1)$$

where:

$wr(BG,b)=10f(BG)^b$ if $f(BG)>0$ and 0 otherwise, where $f$ is a symmetrization function, b=1, representing a weighting parameter, and said computed Dr is mathematically defined as:

$Dr$=average of $s_{k+1}-s_k$, where:

$s_k=10S(k+t_1)^2$ for $k=0, 1, \ldots, t_n-t_1$, $S(t_j)=ff(x_j)$, for $j=1, \ldots, n$, where $x$, is a BG reading of said patient at time 11. The method of claim 8, wherein said estimating $HbA_{1c}$ from said BG monitoring data comprises determining Estimated $HbA_{1c}$ according to:

Estimated $HbA_{1c}$=0.9008(WR)−0.8207(DR)+6.7489.

12. The method of claim 8, further comprising:

defining predetermined categories for the estimate of $HbA_{1c}$, each of said $HbA_{1c}$ estimate categories representing a range of values for estimated $HbA_{1c}$; and assigning said estimated $HbA_{1c}$ to at least one of said $HbA_{1c}$ estimate categories.

13. The method of claim 12, wherein said $HbA_{1c}$ estimate categories are defined as follows:

classified category 1, wherein said estimated $HbA_{1c}$ is less than about 7.8;

classified category 2, wherein said estimated $HbA_{1c}$ is between about 7.8 and about 8.5;

classified category 3, wherein said estimated $HbA_{1c}$ is between about 8.5 and about 9.0;

classified category 4, wherein said estimated $HbA_{1c}$ is between about 9.0 and about 9.6;

classified category 5, wherein said estimated $HbA_{1c}$ is between about 9.6 and about 10.3;

classified category 6, wherein said estimated $HbA_{1c}$ is between about 10.3 and about 11.0; and classified category 7, wherein said estimated $HbA_{1c}$ is above about 11.0.

14. The method of claim 13, further comprising:

defining predicted confidence intervals for corresponding said $HbA_{1c}$ estimate categories, wherein said predicted confidence intervals are defined as follows:

said classified category 1 corresponds with a predicted $HbA_{1c}$ less than about 8.0;

said classified category 2 corresponds with a predicted $HbA_{1c}$ between about 8.0 and about 8.5;

said classified category 3 corresponds with a predicted $HbA_{1c}$ between about 8.5 and about 9.0;

said classified category 4 corresponds with a predicted $HbA_{1c}$ between about 9.0 and about 9.5;

said classified category 5 corresponds with a predicted $HbA_{1c}$ between about 9.5 and about 10.1;

said classified category 6 corresponds with a predicted $HbA_{1c}$ between about 10.1 and about 11.0; and said classified category 7 corresponds with a predicted $HbA_{1c}$ above about 11.0.

15. A system for evaluating hemoglobin $A_{1c}$ ($HbA_{1c}$) of a patient based on blood glucose (BG) data collected over a predetermined duration, said system comprising:

a database component operative to maintain a database identifying said BG data;

a processor programmed to:

compute weighted deviation of the BG of said patient toward high blood glucose (WR) from a predefined normal level;

compute mean blood glucose (Dr) based on said collected BG data; and estimate $HbA_{1c}$ using a predetermined mathematical formula based on said computed WR and Dr; and define predetermined categories for the estimate of $HbA_{1c}$, each of said $HbA_{1c}$ estimate categories representing a range of values for estimated $HbA_{1c}$; and assign said estimated $HbA_{1c}$ to at least one of said $HbA_{1c}$ estimate categories.

16. The system of claim 15, wherein:

said computed WR is mathematically defined from a series of BG readings $x_1, x_2, \ldots x_n$ taken at time points $t_1, t_2, \ldots t_n$ as:

$$WR = \frac{1}{n}\sum_{i=1}^{n} wr(x_i, 1)$$

where:

$wr(BG,b)=10f(BG)^b$ if $f(BG)>0$ and 0 otherwise, where $f$ is a symmetrization function, b=1, representing a weighting parameter, and said computed Dr is mathematically defined as:

$Dr$=average of $s_{k+1}-s_k$, where:

$s_k=10S(k+t_1)^2$ for $k=0, 1, \ldots, t_n-t_1$, $S(t_j)=f(x_j)$, for $j=1, \ldots, n$, where is a BG reading of said patient at time $j$.

17. The system of claim 15, wherein said estimating $HbA_{1c}$ from said BG monitoring data comprises determining Estimated $HbA_{1c}$ according to:

Estimated $HbA_{1c}$=0.9008(WR)−0.8207(DR)+6.7489.

18. The system of claim 15, wherein said $HbA_{1c}$ estimate categories are defined as follows:

classified category 1, wherein said estimated $HbA_{1c}$ is less than about 7.8;

classified category 2, wherein said estimated $HbA_{1c}$ is between about 7.8 and about 8.5;

classified category 3, wherein said estimated $HbA_{1c}$ is between about 8.5 and about 9.0;

classified category 4, wherein said estimated $HbA_{1c}$ is between about 9.0 and about 9.6;

classified category 5, wherein said estimated $HbA_{1c}$ is between about 9.6 and about 10.3;

classified category 6, wherein said estimated $HbA_{1c}$ is between about 10.3 and about 11.0; and classified category 7, wherein said estimated $HbA_{1c}$ is above about 11.0.

19. The system of claim 18, wherein said processor being further programmed to:

define predicted confidence intervals for corresponding said $HbA_{1c}$ estimate categories, wherein said predicted confidence intervals are defined as follows:

said classified category 1 corresponds with a predicted $HbA_{1c}$ less than about 8.0;

said classified category 2 corresponds with a predicted $HbA_{1c}$ between about 8.0 and about 8.5;

said classified category 3 corresponds with a predicted $HbA_{1c}$ between about 8.5 and about 9.0;

said classified category 4 corresponds with a predicted $HbA_{1c}$ between about 9.0 and about 9.5;

said classified category 5 corresponds with a predicted $HbA_{1c}$ between about 9.5 and about 10.1;

said classified category 6 corresponds with a predicted $HbA_{1c}$ between about 10.1 and about 11.0; and said classified category 7 corresponds with a predicted $HbA_{1c}$ above about 11.0.

20. The system of claim 15, wherein said processor being further programmed to:

define predicted confidence intervals for corresponding said $HbA_{1c}$, each of said predicted confidence intervals representing a range of values for $HbA_{1c}$.

21. The system of claim 20, wherein said predicted $HbA_{1c}$ confidence intervals have about a 95% confidence level.

22. A glycemic control system for evaluating hemoglobin $A_{1c}$ ($HbA_{1c}$) of a patient, said system comprising:

a blood glucose (BG) acquisition mechanism, said acquisition mechanism configured to acquire BG data from the patient, a database component operative to maintain a database identifying said BG data; a processor programmed to:

compute weighted deviation of the BG of said patient toward high blood glucose (WR) from a predefined normal level;

compute mean blood glucose (Dr) based on said collected BG data; and estimate $HbA_{1c}$ using a predetermined mathematical formula based on said computed WR and Dr;

define predetermined categories for the estimate of $HbA_{1c}$, each of said $HbA_{1c}$ estimate categories representing a range of values for estimated $HbA_{1c}$; and assign said estimated $HbA_{1c}$ to at least one of said $HbA_{1c}$ estimate categories.

23. The system of claim 22, wherein:

said computed WR is mathematically defined from a series of BG readings $x_1, x_2, \ldots x_n$ taken at time points $t_1, t_2, \ldots t_n$ as:

$$WR = \frac{1}{n}\sum_{i=1}^{n} wr(x_i, 1)$$

where:

$wr(BG, b) = 10f(BG)^b$ if $f(BG) > 0$ and 0 otherwise, where $f$ is a symmetrization function,
$b=1$, representing a weighting parameter, and said computed Dr is mathematically defined as:

$Dr$ = average of $s_{k+1} - s_k$, where:

$s_k = 10S(k+t_1)^2$ for $k = 0, 1, \ldots, t_n - t_1$, $S(t_j) = f(x_j)$, for $j = 1, \ldots, n$, where $x_j$ is a BG reading of said patient at time $j$.

24. The system of claim 22, wherein estimating $HbA_{1c}$ from said BG monitoring data comprises determining Estimated $HbA_{1c}$ according to:

Estimated $HbA_{1c} = 0.9008(WR) - 0.8207(DR) + 6.7489$.

25. The system of claim 22, wherein said $HbA_{1c}$ estimate categories are defined as follows:

classified category 1, wherein said estimated $HbA_{1c}$ is less than about 7.8;

classified category 2, wherein said estimated $HbA_{1c}$ is between about 7.8 and about 8.5;

classified category 3, wherein said estimated $HbA_{1c}$ is between about 8.5 and about 9.0;

classified category 4, wherein said estimated $HbA_{1c}$ is between about 9.0 and about 9.6;

classified category 5, wherein said estimated $HbA_{1c}$ is between about 9.6 and about 10.3;

classified category 6, wherein said estimated $HbA_{1c}$ is between about 10.3 and about 11.0; and classified category 7, wherein said estimated $HbA_{1c}$ is above about 11.0.

26. The system of claim 25, wherein:

said processor programmed to:

define predicted confidence intervals for corresponding said $HbA_{1c}$ estimate categories, wherein said predicted confidence intervals are defined as follows:

said classified category 1 corresponds with a predicted $HbA_{1c}$ less than about 8.0;

said classified category 2 corresponds with a predicted $HbA_{1c}$ between about 8.0 and about 8.5;

said classified category 3 corresponds with a predicted $HbA_{1c}$ between about 8.5 and about 9.0;

said classified category 4 corresponds with a predicted $HbA_{1c}$ between about 9.0 and about 9.5;

said classified category 5 corresponds with a predicted $HbA_{1c}$ between about 9.5 and about 10.1;

said classified category 6 corresponds with a predicted $HbA_{1c}$ between about 10.1 and about 11.0; and said classified category 7 corresponds with a predicted $HbA_{1c}$ above about 11.0.

27. The system of claim 22, wherein:

said processor programmed to:

define predicted confidence intervals for corresponding said $HbA_{1c}$, each of said predicted confidence intervals representing a range of values for $HbA_{1c}$.

28. The system of claim 27, wherein said predicted $HbA_{1c}$ confidence intervals have about a 95% confidence level.

29. A computer program product comprising a computer useable medium having computer program logic for enabling at least one processor in a computer system to evaluate hemoglobin $A_{1c}$ ($HbA_{1c}$) of a patient based on blood glucose (BG) data, said computer program logic comprising:

computing weighted deviation of the BG of said patient toward high blood glucose (WR) from a predefined normal level;

computing mean blood glucose (Dr) based on said collected BG data; and estimating $HbA_{1c}$ using a predetermined mathematical formula based on said computed WR and Dr; and providing a predetermined confidence interval for classification of said estimated value of $HbA_{1c}$, wherein said confidence interval is a single value or a range of values.

30. A glycemic control system for evaluating hemoglobin $A_{1c}$ ($HbA_{1c}$) of a patient, said system comprising:
a blood glucose (BG) acquisition mechanism, said acquisition mechanism configured to acquire BG data from the patient,
a database component operative to maintain a database identifying said BG data;
a processor programmed to:
compute weighted deviation of the BG of said patient toward high blood glucose (WR) from a predefined normal level and estimated rate of change of blood glucose (Dr) based on said collected BG data; and
estimate $HbA_{1c}$ using a predetermined mathematical formula based on said computed WR and Dr, wherein:
said computed WR is mathematically defined from a series of BG readings $x_1, x_2, \ldots x_n$ taken at time points $t_1, t_2, \ldots t_n$ as:

$$WR = \frac{1}{n}\sum_{i=1}^{n} wr(x_i, 1)$$

where:

$wr(BG,b)=10f(BG)^b$ if $f(BG)>0$ and 0 otherwise, where $f$ is a symmetrization function,
b=1, representing a weighting parameter, and
said computed DR is mathematically defined as:

$Dr$=average of $s_{k+1}-s_k$, where:

$s_k=10S(k+t_1)^2$ for $k=0, 1, \ldots, t_n-t_1$, $S(t_j)=f(x_j)$, for $j=1, \ldots, n$, where $x_j$ is a BG reading of said patient at time $j$.

31. A glycemic control system for evaluating hemoglobin $A_{1c}$ ($HbA_{1c}$) of a patient, said system comprising:
a blood glucose (BG) acquisition mechanism, said acquisition mechanism configured to acquire BG data from the patient,
a database component operative to maintain a database identifying said BG data;
a processor programmed to:
compute weighted deviation of the BG of said patient toward high blood glucose (WR) from a predefined normal level and estimated rate of change of blood glucose (Dr) based on said collected BG data; and
estimate $HbA_{1c}$ using a predetermined mathematical formula based on said computed WR and Dr, wherein said estimating $HbA_{1c}$ from said BG monitoring data comprises determining Estimated $HbA_{1c}$ according to:

Estimated $HbA_{1c}$=0.9008(WR)−0.8207(DR)+6.7489.

32. A glycemic control system for evaluating hemoglobin $A_{1c}$ ($HbA_{1c}$) of a patient, said system comprising:
a blood glucose (BG) acquisition mechanism, said acquisition mechanism configured to acquire BG data from the patient,
a database component operative to maintain a database identifying said BG data;
a processor programmed to:
compute weighted deviation of the BG of said patient toward high blood glucose (WR) from a predefined normal level and estimated rate of change of blood glucose (Dr) based on said collected BG data;
estimate $HbA_{1c}$ using a predetermined mathematical formula based on said computed WR and Dr;
define predetermined categories for the estimate of $HbA_{1c}$, each of said $HbA_{1c}$ estimate categories representing a range of values for estimated $HbA_{1c}$; and
assign said estimated $HbA_{1c}$ to at least one of said $HbA_{1c}$ estimate categories.

33. The system of claim 32, wherein said $HbA_{1c}$ estimate categories are defined as follows:
classified category 1, wherein said estimated $HbA_{1c}$ is less than about 7.8;
classified category 2, wherein said estimated $HbA_{1c}$ is between about 7.8 and about 8.5;
classified category 3, wherein said estimated $HbA_{1c}$ is between about 8.5 and about 9.0;
classified category 4, wherein said estimated $HbA_{1c}$ is between about 9.0 and about 9.6;
classified category 5, wherein said estimated $HbA_{1c}$ is between about 9.6 and about 10.3;
classified category 6, wherein said estimated $HbA_{1c}$ is between about 10.3 and about 11.0; and
classified category 7, wherein said estimated $HbA_{1c}$ is above about 11.0.

34. The system of claim 33, wherein:
said processor programmed to:
define predicted confidence intervals for corresponding said $HbA_{1c}$ estimate categories, wherein said predicted confidence intervals are defined as follows:
said classified category 1 corresponds with a predicted $HbA_{1c}$ less than about 8.0;
said classified category 2 corresponds with a predicted $HbA_{1c}$ between about 8.0 and about 8.5;
said classified category 3 corresponds with a predicted $HbA_{1c}$ between about 8.5 and about 9.0;
said classified category 4 corresponds with a predicted $HbA_{1c}$ between about 9.0 and about 9.5;
said classified category 5 corresponds with a predicted $HbA_{1c}$ between about 9.5 and about 10.1;
said classified category 6 corresponds with a predicted $HbA_{1c}$ between about 10.1 and about 11.0; and
said classified category 7 corresponds with a predicted $HbA_{1c}$ above about 11.0.

35. The system of claim 32, wherein:
said processor programmed to:
define predicted confidence intervals for corresponding said $HbA_{1c}$, each of said predicted confidence intervals representing a range of values for $HbA_{1c}$.

36. The system of claim 35, wherein said predicted $HbA_{1c}$ confidence intervals have about a 95% confidence level.

* * * * *